United States Patent
Georgiou et al.

(10) Patent No.: US 11,542,486 B2
(45) Date of Patent: Jan. 3, 2023

(54) HUMAN KYNURENINASE ENZYME VARIANTS HAVING IMPROVED PHARMACOLOGICAL PROPERTIES

(71) Applicant: Board of Regents, the University of Texas System, Austin, TX (US)

(72) Inventors: George Georgiou, Austin, TX (US); Everett Stone, Austin, TX (US); John Blazeck, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 145 days.

(21) Appl. No.: 16/081,492

(22) PCT Filed: Mar. 2, 2017

(86) PCT No.: PCT/US2017/020355
§ 371 (c)(1),
(2) Date: Aug. 31, 2018

(87) PCT Pub. No.: WO2017/151860
PCT Pub. Date: Sep. 8, 2017

(65) Prior Publication Data
US 2021/0207110 A1    Jul. 8, 2021

Related U.S. Application Data

(60) Provisional application No. 62/302,306, filed on Mar. 2, 2016.

(51) Int. Cl.
| | |
|---|---|
| C12N 9/14 | (2006.01) |
| A61K 47/60 | (2017.01) |
| A61P 35/00 | (2006.01) |
| A61K 35/17 | (2015.01) |
| A61K 38/46 | (2006.01) |
| A61K 39/395 | (2006.01) |
| C12N 9/96 | (2006.01) |

(52) U.S. Cl.
CPC ............ *C12N 9/14* (2013.01); *A61K 35/17* (2013.01); *A61K 38/46* (2013.01); *A61K 39/3955* (2013.01); *A61K 47/60* (2017.08); *A61P 35/00* (2018.01); *C12N 9/96* (2013.01); *C12Y 307/01003* (2013.01)

(58) Field of Classification Search
None
See application file for complete search history.

(56) References Cited

U.S. PATENT DOCUMENTS

| | | | |
|---|---|---|---|
| 7,109,304 B2 | 9/2006 | Hansen et al. | |
| 7,714,139 B2 | 5/2010 | Prendergast et al. | |
| 8,377,976 B2 | 2/2013 | Combs et al. | |
| 8,465,743 B2 | 6/2013 | Rosenberg et al. | |
| 9,808,486 B2 | 11/2017 | Georgiou et al. | |
| 9,975,959 B2 | 5/2018 | Georgiou et al. | |
| 10,772,913 B2 | 9/2020 | Georgiou et al. | |
| 11,168,142 B2 * | 11/2021 | Georgiou | ........... C07K 16/2896 |
| 2003/0194721 A1 | 10/2003 | Mikita et al. | |
| 2009/0304666 A1 | 12/2009 | Harrison | |
| 2015/0064154 A1 | 3/2015 | Georgiou et al. | |
| 2016/0058845 A1 | 3/2016 | Georgiou et al. | |
| 2017/0056449 A1 | 3/2017 | Georgiou et al. | |
| 2019/0002579 A1 | 1/2019 | Georgiou et al. | |
| 2019/0350975 A1 | 11/2019 | Georgiou et al. | |
| 2020/0054674 A1 | 2/2020 | Georgiou et al. | |
| 2021/0213059 A1 | 7/2021 | Georgiou et al. | |

FOREIGN PATENT DOCUMENTS

| | | |
|---|---|---|
| CN | 1442487 | 9/2003 |
| JP | 2008-237022 | 10/2008 |
| JP | 2010-504346 | 2/2010 |
| JP | 2006-521378 | 11/2016 |
| JP | 2016-533753 | 11/2016 |
| KR | 10-2012-0085209 | 7/2012 |
| WO | WO 2003/065984 | 8/2003 |
| WO | WO 2007/004692 | 1/2007 |
| WO | WO 2012/031744 | 3/2012 |
| WO | WO 2012/079000 | 6/2012 |
| WO | WO 2012/099441 | 7/2012 |
| WO | WO 2013/034685 | 3/2013 |
| WO | WO 2013/059593 | 4/2013 |
| WO | WO 2015/031771 | 3/2015 |
| WO | WO 2016/033488 | 3/2016 |

(Continued)

OTHER PUBLICATIONS

Pilotte, Luc et al. "Reversal of tumoral immune resistance by inhibition of tryptophan 2,3-dioxygenase." Proceedings of the National Academy of Sciences of the United States of America vol. 109,7 (2012): 2497-502. doi:10.1073/pnas.1113873109 (Year: 2018).*
"KYNU_Human," UniProt Submission Q16719, dated Jul. 24, 2013.
"Kynureninase (EC 3.7.1.3)—human", GenBank accession No. G02652, 1999.
"SIDS2vsH1YAV1," UniProt 201609, dated Mar. 21, 2012.
Adams et al. "The kynurenine pathway in brain tumor pathogenesis." *Cancer Research* 72.22 (2012): 5649-5657.
Alberati-Giani et al., "Isolation and expression of a cDNA clone encoding human kynureninase", *Eur. J. Biochem.*, 239(2):460-468, 1996.
Chen and Guillemin, "Kynurenine pathway metabolites in humans: disease and healthy states," *Int. J. Tryptophan Res.*, 2:1-19, 2009.

(Continued)

*Primary Examiner* — Michael Szperka
*Assistant Examiner* — Lia E Taylor
(74) *Attorney, Agent, or Firm* — Parker Highlander PLLC

(57) ABSTRACT

Methods and compositions related to the use of a protein with kynureninase activity are described. For example, in certain aspects there may be disclosed a modified kynureninase capable of degrading kynurenine. Furthermore, certain aspects of the invention provide compositions and methods for the treatment of cancer with kynurenine depletion using the disclosed proteins or nucleic acids.

13 Claims, 3 Drawing Sheets
Specification includes a Sequence Listing.

(56) References Cited

FOREIGN PATENT DOCUMENTS

| WO | WO 2017/151860 | 9/2017 |
| WO | WO 2019/204269 | 10/2019 |

OTHER PUBLICATIONS

Curran et al., "PD-1 and CTLA-4 combination blockade expands infiltrating T cells and reduces regulatory T and myeloid cells within B16 melanoma tumors," *Proc. Natl. Acad. Sci. U S A*, 107:4275-4280, 2010.

de Jong et al., "Serum tryptophan and kynurenine concentrations as parameters for indoleamine 2,3-dioxygenase activity in patients with endometrial, ovarian, and vulvar cancer," *Int. J. Gynecol. Cancer*, 21(7):1320-1327, 2011.

Della Chiesa et al., "The tryptophan catabolite L-kynurenine inhibits the surface expression of NKp46-and NKG2D-activating receptors and regulates NK-cell function," *Blood*, 108(13):4118-4125, 2006.

Disis et al., "Use of tumor-responsive T cells as cancer treatment", *Lancet*, 373:673-683, 2009.

Duval et al., "Adoptive transfer of allogenic cytotoxic T lymphocytes equipped with a HLA-A2 restricted MART-1 T-cell receptor: a phase I trial in metastatic melanoma", *Clin. Cancer Res.*, 12:1229-1236, 2006.

Extended European Search Report issued in corresponding European Application No. 17760774, dated Jul. 22, 2019.

Extended European Search Report issued in corresponding European Application No. 18204264, dated Apr. 25, 2019.

Extended European Search Report issued in European Patent Application No. 14840339.7, dated Mar. 28, 2017.

Gailani et al., "Studies on tryptophan metabolism in patients with bladder cancer," *Cancer Research.*, 33: 1071-1077, 1973.

Godin-Ethier et al., "Indoleamine 2, 3-Dioxygenase Expression in Human Cancers: Clinical and Immunologic Perspectives," *Clinical Cancer Research*, 17(22):6985-6991, 2011.

Holmgaard et al., "Indoleamine 2, 3-dioxygenase is a critical resistance mechanism in antitumor T cell immunotherapy targeting CTLA-4," *The Journal of Experimental Medicine*, 210:1389-1402, 2013.

Hoyos et al., "Genetic modification of human T lymphocytes for the treatment of hematological malignancies", *Haematologica*, 97(11):1622-1631, 2012.

International Preliminary Report on Patentability issued in corresponding PCT Application No. PCT/US2017/020355, dated Sep. 13, 2018.

International Preliminary Report on Patentability issued in International Application No. PCT/US2014/053437, dated Mar. 10, 2016.

International Preliminary Report on Patentability issued in International Application No. PCT/US2015/047475, dated Mar. 9, 2017.

International Search Report and Written Opinion issued in corresponding PCT Application No. PCT/US2017/020355, dated Aug. 2, 2017.

International Search Report and Written Opinion issued in International Application No. PCT/US2014/053437, dated Mar. 10, 2015.

International Search Report and Written Opinion issued in International Application No. PCT/US2015/047475, dated Feb. 2, 2016.

International Search Report and Written Opinion issued in PCT Application No. PCT/US2019/027623, dated Aug. 22, 2019.

Kaper et al., "Nanosensor detection of an immunoregulatory tryptophan influx/kynurenine efflux cycle," *PLoS Biology*, 5(10):e257, 2007.

Lima et al., "Crystal Structure of *Homo sapiens* Kynureninase", *Biochemistry*, 46(10):2735-2744, 2007.

Lima et al., "Crystal Structure of the *Homo sapiens* Kynureninase-3-Hydroxyhippuric Acid Inhibitor Complex: Insights into the Molecular Basis Of Kynureninase Substrate Specificity", *J. Med. Chem.*, 52(2):389-396, 2009.

Lipowska-Bhalla et al., "Targeted immunotherapy of cancer with CAR T cells: achievements and challenges," *Cancer Immunology Immunotherapy*, 61(7):953-962, 2012.

Lob et al., "Inhibitors of indoleamine-2,3-dioxygenase for cancer therapy: can we see the wood for the trees?" *Nat. Rev. Cancer*, 9(6):445-452, 2009.

Mandi and Vecsei, "The kynurenine system and immunoregulation," *J. Neural Transm.*, 119(2):197-209, 2012.

Mezrich et al., "An interaction between kynurenine and the aryl hydrocarbon receptor can generate regulatory T cells," *The Journal of Immunology*, 185(6):3190-3198, 2010.

Office Communication issued in Chinese Application No. 201480053899.1, dated Feb. 15, 2019. (English Translation).

Office Communication issued in corresponding Japanese Application No. 2016-537898, dated Sep. 20, 2017. (English Translation).

Office Communication issued in Japanese Application No. 2017-511675, dated Jun. 27, 2019. (English Translation).

Office Communication issued in Japanese Application No. 2018-042760, dated Jan. 16, 2019. (English Translation).

Office Communication Issued in U.S. Appl. No. 14/473,040, dated Nov. 23, 2016.

Office Communication issued in U.S. Appl. No. 14/839,293, dated Jan. 6, 2017.

Office Communication issued in U.S. Appl. No. 15/351,060, dated Dec. 12, 2016.

Office Communication issued in U.S. Appl. No. 14/839,293, dated Oct. 19, 2017.

Office Communication issued in U.S. Appl. No. 14/839,293, dated Apr. 14, 2017.

Office Communication issued in U.S. Appl. No. 14/473,040, dated Jul. 3, 2017.

Office Communication issued in U.S. Appl. No. 14/473,040, dated Jul. 6, 2016.

Office Communication issued in U.S. Appl. No. 15/351,060, dated Mar. 9, 2018.

Office Communication issued in U.S. Appl. No. 15/351,060, dated Jun. 26, 2017.

Opitz et al., "An endogenous tumour-promoting ligand of the human aryl hydrocarbon receptor," *Nature*, 478(7368):197-203, 2011.

Opitz et al., "The Indoleamine-2, 3-Dioxygenase (IDO) Inhibitor 1-Methyl-D-tryptophan Upregulates IDO1 in Human Cancer Cells," *PLoS One*, 6(5):e19823, 2011.

Phillips, "Structure and mechanism of kynurinase", *Arch. Biochem. Biophys.*, 544:69-74, 2014.

Phillips, "Structure, mechanism, and substrate specificity of kynureninase", *Biochimica et Biophysica Acta*, 1814: 1481-1488, 2011.

Pilotte et al., "Reversal of tumoral immune resistance by inhibition of tryptophan 2,3-dioxygenase," *Proc. Natl. Acad. Sci. U S A*, 109(7):2497-2502, 2012.

Platten et al., "Cancer Immunotherapy by Targeting IDO1/TDO and Their Downstream Effect", *Front. Immunol.*, 5:673, 2015.

Prendergast, "Cancer: Why tumours eat tryptophan," *Nature*, 478(7368):192-194, 2011.

Rabinkov et al., "Alliinase: structural peculiarities and applying for targeted therapy: SW02. W10-4", *FEBS J.*, 280.1, 2013.

Response filed in U.S. Appl. No. 14/839,293, dated Mar. 6, 2017.

Rutella et al., "Targeting indoleamine 2,3-dioxygenase (IDO) to counteract tumour-induced immune dysfunction: from biochemistry to clinical development," *Endocr. Metab. Immune Disord. Drug Targets*, 9(2):151-177, 2009.

Schottler et al., "Protein engineering of the restriction endonuclease EcoRV—structure-guided design of enzyme variants that recognize the base pairs flanking the recognition site", *eur. J. Biochem.*, 258(1):184-191, 1998.

Shin et al., "Modulation of natural killer cell antitumor activity by the aryl hydrocarbon receptor," *Proc. Natl. Acad. Sci. U S A*, 110(30):12391-12396, 2013.

Simpson et al., "Fc-dependent depletion of tumor-infiltrating regulatory T cells co-defines the efficacy of anti-CTLA-4 therapy against melanoma," *J. Exp. Med.*, 210(9): 1695-1710, 2013.

(56) References Cited

OTHER PUBLICATIONS

Song et al., "L-Kynurenine-induced apoptosis in human NK cells is mediated by reactive oxygen species," *International Immunopharmacology*, 11(8):932-938, 2011.

Stone et al., "Abstract LB-226: Depletion of kynurenine using an engineered therapeutic enzyme potently inhibits cancer immune checkpoints both as a monotherapy and in combination with anti-PD-1," Proceedings of the AACR 106th Annual Meeting, Philadelphia, PA, Apr. 18-22, 2015, Cancer *Research*, 75(15 Supplement):LB-226-LB-226, Aug. 2015.

Supplementary European Search Report issued in European Patent Application No. 15834988.6, dated Jan. 16, 2018.

Toma et al., "Cloning and recombinant expression of rat and human kynureninase", *FEBS Lett.*, 408(1):5-10, 1997.

Veronese et al., "Peptide and protein PEGylation: a review of problems and solutions," *Biomaterials*, 22(5): 405-417, 2001.

Walsh et al., "Purification and biochemical characterization of some of the properties of recombinant human kynurinase", *Eur. J. Biochem.*, 269:2069-2074, 2002.

Yao et al., "Serum metabolic profiling and features of papillary thyroid carcinoma and nodular goiter," *Mol. Biosyst.*, 7(9):2608-2614, 2011.

Yoshikawa et al., "Serum concentration of L-kynurenine predicts the clinical outcome of patients with diffuse large B-cell lymphoma treated with R-CHOP," *Eur. J. Haematol.*, 84(4):304-309, 2010.

"Kynureninase (L-kynurenine hydrolase) variant", GenBank: BAD97146.1, dated Apr. 26, 2005.

Akash et al., "Development of therapeutic proteins: advances and challenges," Tuk. J. Biol., 39:343-358, 2015.

Aznar et al., "Intratumoral delivery of immunotherapy—Act Locally, Think Globally," J. Immunol., 198:31-39, 2017.

Baghban et al., "Tumor microenvironment complexity and therapeutic implications at a glance," Cell Communication and Signaling, 18:1-19, 2020.

KR 10-2012-0085209, Machine Translation from Korean Intellectual Property Office, downloaded on Jun. 25, 2021, from http://engpat.kipris.or.kr/pmt/patent/patentRTT.jsp.

Marabelle et al., "Intratumoral immunotherapy: using the tumor as the remedy," Annals of Oncology, 28:xii33-xii43, 2017.

Shanks et al., "Are animal models predictive for humans?" Philosophy, Ethics, and Humanities in Medicine, 4:2, 2009.

Singh et al., "Protein Engineering Approaches in the Post-Genomic Era," Current Protein and Peptide Science, 18:1-11, 2017.

Sutradhar et al. "Distribution and elimination of protein therapeutics: A review," S. J. Pharm. Sci., 4:1-12, 2011.

Triplett et al., "Reversal of IDO-mediated cancer immune suppression by systemic kynurenine depletion with a therapeutic enzyme," Nat. Biotechnol., 36:758-764, 2018.

UniProt_201609 Acc#H1YAV1 Lucas et al., Mar. 21, 2012. Alignment with SEQ ID No. 33.

Zhang et al., "Propagated Perturbations from a Peripheral Mutation Show Interactions Supporting WW Domain Thermostability," Structure, 26:1474-1485, 2018.

* cited by examiner

US 11,542,486 B2

HUMAN KYNURENINASE ENZYME VARIANTS HAVING IMPROVED PHARMACOLOGICAL PROPERTIES

This application is a national phase application under 35 U.S.C. § 371 of International Application No. PCT/US2017/020355, filed Mar. 2, 2017, which claims the benefit of U.S. Provisional Patent Application No. 62/302,306, filed Mar. 2, 2016, the entirety of each of which is incorporated herein by reference.

The invention was made with government support under Grant No. R01 CA154754 awarded by the National Institutes of Health and by CPRIT grant DP150061 from the State of Texas. The U.S. government and the State of Texas have certain rights in the invention.

BACKGROUND OF THE INVENTION

1. Field of the Invention

The invention generally relates to compositions and methods for the treatment of cancer with enzymes that deplete L-kynurenine or L-3-hydroxykynurenine. More particularly, it concerns the engineering, pharmacological optimization and use of bacterial and human enzymes with L-kynurenine degrading activity suitable for human therapy.

2. Description of Related Art

Overexpression of indolamine-2,3-dioxygenase isoforms (IDO1 or IDO2) by cancer cells or reprogramming of cancer infiltrating leukocytes to express either of these enzymes has been shown to have a profound effect on attenuating adaptive immune responses to cancer. IDO1 and IDO2 as well as the enzyme tryptophan 2,3-dioxygenase (TDO), whose expression by stromal cells may be induced by some tumors, catalyze the rate limiting step in tryptophan (Trp) catabolism to L-kynurenine (KYN). Tumors exchange a cytosolic KYN molecule for an extracellular Trp molecule using a LAT1-like amino acid exchanger (Kaper et al., 2007), which has the dual effect on immune cells of locally elevating levels of KYN while locally depleting Trp levels. Neighboring immune cells internalize KYN, where it is an activating ligand for the aryl hydrocarbon receptor (AHR) resulting in the expression of numerous cytokines and chemokines that lead to tumor tolerance through immune cell differentiation and/or induction of apoptosis (Della Chiesa et al., 2006; Opitz et al., 2011; Song et al., 2011). Additionally, other KYN-related compounds formed from kynurenine, most notably kynurenic acid also exert an immunosuppressive effect by serving as agonists of the orphan GPCR GPCR35. Inhibition of KYN formation and, thus, inhibition of the formation of KYN metabolism byproducts, including kynurenic acid, 3-hydroxyl kynurenine and quinolinic acid, via the inhibition of IDO1 or TDO has received a significant amount of attention as a cancer target (Chen and Guillemin, 2009; Rutella et al., 2009; Prendergast, 2011). Substrate analog inhibitors, such as 1-DL-methyltryptophan, for IDO1 have been developed and have shown initial promise in overcoming cancer induced tumor tolerance thus restoring the ability of the native immune system to fight tumors (Lob et al., 2009). However, KYN is also produced by tryptophan 2,3-dioxygenase (TDO), which is also frequently expressed in tumors and this enzyme is not inhibited by 1-DL-methyltryptophan (Pilotte et al., 2012).

Controlling tumor production of KYN is the focus of much research and has the potential to treat, among others, cancers such as breast cancer, ovarian, glioblastoma, and pancreatic carcinoma. KYN is known to suppress proliferation as well as induce apoptosis in T cells and NK cells (Opitz et al., 2011; Mandi and Vacsei, 2012) enabling tumors to evade detection and destruction by a patient's immune system. KYN is a potent ligand of the aryl hydrocarbon receptor (AHR) whose activation in T cells induces differentiation into CD25$^+$FoxP3$^+$ T regulatory cells (Tregs) (Mezrich et al., 2010). KYN has also been shown to prevent cytokine mediated up-regulation of specific receptors (NKp46 and NKG2D) required for NK mediated cell killing tumor cell lines (Della Chiesa et al., 2006), an action that is also likely mediated by its agonistic effect on AHR (Shin et al., 2013). There is also clinical evidence linking elevated serum KYN levels and decreased survival in multiple types of cancer. In healthy patients, KYN levels in serum are in the range of 0.5 to 1 µM. In patients with cancer types that produce KYN, such as diffuse large B-cell lymphoma, serum KYN levels were measured to be as much as 10 times higher (Yoshikawa et al., 2010; de Jong et al., 2011; Yao et al., 2011) and were prognostic for survival among lymphoma patients receiving the same treatment regimen; those with serum levels below 1.5 µM exhibited a 3 year survival rate of 89%, compared to only 58% survival for those with KYN levels above 1.5 µM. This difference in survival was attributed to the immune suppressing effects of KYN (Yoshikawa et al., 2010).

The present invention discloses the use of enzymes for the specific depletion of KYN and its metabolites in tumors and/or in the blood. KYN depleting enzymes are used to lower KYN concentrations for the treatment of tumors expressing IDO1, IDO2, or TDO, thus preventing tumor-mediated tolerogenic effects and instead mediating tumor-ablating pro-inflammatory responses. Notably, the use of enzymes for the depletion of KYN and KYN metabolic byproducts circumvents the problems associated with small molecule inhibitors of IDO isoforms and TDO discussed above and further completely circumvents off target effects that are very commonly accompany small molecule drugs and lead to unpredicted toxicities and side effects.

SUMMARY OF THE INVENTION

For therapeutic applications the use of the *Homo sapiens* Kynureninase enzyme may be preferable. Being a native enzyme the *Homo sapiens* Kynureninase is expected to be subject to tolerance in humans and thus to be unlikely to elicit immune responses, including the production of anti-*Homo sapiens* Kynureninase antibodies, when used as a therapeutic. However the *Homo sapiens* Kynureninase preferentially degrades the KYN derivative 3'OH Kynurenine (3'OH KYN). The *Homo sapiens* Kynureninase (h-KYNase) shows catalytic activity for the degradation of KYN that is about 1,000 fold lower than the activity of some bacterial enzymes such as the enzyme from *Pseudomonas* fluorescence (PCT/US2014/053437). While bacterial enzymes such as those produced by *Pseudomonas* fluorescence or by *Mucilaginibacter paludis* have high catalytic activity for the degradation of KYN that has been shown to result in potent anti-tumor effects in mouse model, these enzymes are not of human origin and thus have a possibility of stimulating adverse immune responses which are detrimental for clinical applications. There is a significant need to develop variants of the *Homo sapiens* Kynureninase having high catalytic activity towards KYN and also a high degree (>65%) of amino acid sequence identity with the *Homo sapiens* enzyme.

Aspects of the present invention overcome a major deficiency in the art by providing enzymes that comprise bacterial or human polypeptide sequences capable of degrading L-kynurenine, having a high degree of sequence identity with the human enzyme to avoid the elicitation of adverse immune responses and displaying favorable pharmacokinetics in serum as desired for cancer therapy. In PCT/US2014/053437, the inventors disclosed mutant h-KYNase enzymes having up to 24-fold higher catalytic efficiency for the degradation of KYN relative to the wild-type human enzyme. There is a need for the discovery of mutant h-KYNase enzymes having higher catalytic activity than those disclosed in PCT/US2014/053437. The present invention addresses this need and discloses mutant enzymes having higher catalytic efficiencies and also mutant enzymes having higher catalytic activity than the wild type h-KYNase and different amino acid substitutions than the variants disclosed in PCT/US2014/053437.

In other aspects, there are provided polypeptides comprising either a native or modified human or primate kynureninase capable of degrading KYN. In some embodiments, the polypeptides are capable of degrading KYN under physiological conditions. For example, the polypeptides have a catalytic efficiency for KYN ($k_{cat}/K_M$) of at least or about 0.01, 0.05, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$ $M^{-1}s^{-1}$ or any range derivable therein.

A modified polypeptide as discussed above may be characterized as having a certain percentage of identity as compared to an unmodified polypeptide (e.g., a native polypeptide) or to any polypeptide sequence disclosed herein. For example, the unmodified polypeptide may comprise at least, or up to, about 150, 200, 250, 300, 350, 400 residues (or any range derivable therein) of a native kynureninase. The percentage identity may be about, at most or at least 65%, 70%, 75%, 80%, 85%, 90%, 95%, 96%, 97%, 98%, or 99% (or any range derivable therein) between the modified and unmodified polypeptides, or between any two sequences in comparison. It is also contemplated that percentage of identity discussed above may relate to a particular modified region of a polypeptide as compared to an unmodified region of a polypeptide. For instance, a polypeptide may contain a modified or mutant substrate recognition site of a kynureninase that can be characterized based on the identity of the amino acid sequence of the modified or mutant substrate recognition site of the kynureninase to that of an unmodified or mutant kynureninase from the same species or across the species. A modified or mutant human polypeptide characterized, for example, as having at least 90% identity to an unmodified kynureninase means that at least 90% of the amino acids in that modified or mutant human polypeptide are identical to the amino acids in the unmodified polypeptide.

Such an unmodified polypeptide may be a native kynureninase, particularly a human isoform or other primate isoforms. For example, the native human kynureninase may have the sequence of SEQ ID NO: 1. Non-limiting examples of other native primate kynureninase include *Pongo abelii* kynureninase (Genbank ID: XP_009235962.1, GI: 686708656), *Macaca fascicularis* kynureninase (Genbank ID: EHH54849.1, GI: 355750522), and Pan troglodytes kynureninase (Genbank ID: XP_003309314.1, GI: 332814521). Exemplary native polypeptides include a sequence having about, at most or at least 65%, 70%, 75%, 80%, 85%, 90%, 95%, 96%, 97%, 98%, 99% or 100% identity (or any range derivable therein) of SEQ ID NO:1. For example, the native polypeptide may comprise at least or up to about 10, 20, 30, 40, 50, 60, 70, 80, 90, 100, 150, 200, 250, 300, 350, 400, 415 residues (or any range derivable therein) of the sequence of SEQ ID NO:1.

In some embodiments, the native *Homo sapiens* kynureninase (h-KYNase) is modified by one or more other modifications, such as chemical modifications, substitutions, insertions, deletions, and/or truncations. For example, the modifications are at a substrate recognitions site of the native enzyme. In a particular embodiment, the native kynureninase is modified by substitutions. For example, the number of substitutions may be one, two, three, four or more. In further embodiments, the native kynureninase is modified in the substrate recognition site or any location that may affect substrate specificity.

Accordingly, in preferred embodiments, the present invention is directed to an isolated, modified human kynureninase enzyme, said modified enzyme having at least one of the following substitutions relative to native human kynureninase (see SEQ ID NO: 1), said substitutions including i) A436T and ii) S408N or F306L, and wherein the modified enzyme comprises a mutation set selected from the group consisting of the following mutation sets: (a) A99I, G112A, F306Y, I331N, I405L, S408N and A436T; (b) A99I, G112A, K191E, F306Y, A381S, I405L, S408N and A436T; (c) Q14R, A99I, G112A, M189I, H230Y, F306Y, I331N, I405L, S408N and A436T; (d) T138S, H224N, F225Y, F306W, N333T, S408N and A436T; (e) N67D, L72N, E103Q, F225Y, I331V, S408N and A436T; (f) N67D, A136S, T138S, F225Y, S408N and A436T; and (g) A99S, A136G, L137T, F306L and A436T.

In more particular aspects, the invention is directed specifically to a modified enzyme that comprises at least the mutation set A99I, G112A, F306Y, I331N, I405L, S408N and A436T. An even more preferred enzyme in this regard is that comprising SEQ ID NO:2.

Another preferred enzyme is thus a modified enzyme that comprises at least the mutation set A99I, G112A, K191E, F306Y, A381S, I405L, S408N and A436T. And, particularly preferred are modified enzymes that comprise SEQ ID NO:3.

Another preferred enzyme comprises at least the mutation set Q14R, A99I, G112A, M189I, H230Y, F306Y, I331N, I405L, S408N and A436T and, particularly preferred are those comprising SEQ ID NO:4.

In still further embodiments, preferred enzymes comprises at least the mutation set T138S, H224N, F225Y, F306W, N333T, S408N and A436T, and particularly preferred are those comprising SEQ ID NO:5.

Further preferred embodiments are directed to enzymes that comprise at least the mutation set N67D, L72N, E103Q, F225Y, I331V, S408N and A436T. And, particularly preferred in this regard are enzymes that comprise SEQ ID NO:6.

And, still further preferred enzymes are those that comprise at least the mutation set N67D, A136S, T138S, F225Y, S408N and A436T. And, particularly preferred such enzymes comprise SEQ ID NO:7.

And, still further preferred enzymes comprise at least the mutation set A99S, A136G, L137T, F306L and A436T. And, particularly preferred enzymes in this regard comprise SEQ ID NO:8.

In some aspects, the present invention also contemplates polypeptides comprising a kynureninase linked to a heterologous amino acid sequence. For example, the kynureninase may be linked to the heterologous amino acid sequence as a fusion protein. In a particular embodiment, the kynureninase is linked to amino acid sequences, such as an IgG Fc, albumin, an albumin binding protein, or an XTEN polypeptide for increasing the in vivo half-life.

To increase serum persistence, the kynureninase may be linked to one or more polyether molecules. In a particular embodiment, the polyether is polyethylene glycol (PEG). The polypeptide may be linked (e.g., covalently) to PEG via specific amino acid residues, such as lysine or cysteine. For therapeutic administration, such a polypeptide comprising the kynureninase may be dispersed in a pharmaceutically acceptable carrier.

In some aspects, a nucleic acid encoding such a kynureninase is contemplated. In some embodiments, the nucleic acid has been codon optimized for expression in bacteria. In particular embodiments, the bacteria are *E. coli*. In other aspects, the nucleic acid has been codon optimized for expression in fungus (e.g., yeast), insects, or mammals. The present invention further contemplates vectors, such as expression vectors, containing such nucleic acids. In particular embodiments, the nucleic acid encoding the kynureninase is operably linked to a promoter, including but not limited to heterologous promoters. In one embodiment, a kynureninase is delivered to a target cell by a vector (e.g., a gene therapy vector). Such viruses may have been modified by recombinant DNA technology to enable the expression of the kynureninase-encoding nucleic acid in the target cell. These vectors may be derived from vectors of non-viral (e.g., plasmids) or viral (e.g., adenovirus, adeno-associated virus, retrovirus, lentivirus, herpes virus, or vaccinia virus) origin. Non-viral vectors are preferably complexed with agents to facilitate the entry of the DNA across the cellular membrane. Examples of such non-viral vector complexes include the formulation with polycationic agents which facilitate the condensation of the DNA and lipid-based delivery systems. An example of a lipid-based delivery system would include liposome based delivery of nucleic acids.

In still further aspects, the present invention further contemplates host cells comprising such vectors. The host cells may be bacteria (e.g., *E. coli*), fungal cells (e.g., yeast), insect cells, or mammalian cells.

In some embodiments, the vectors are introduced into host cells for expressing the kynureninase. The proteins may be expressed in any suitable manner. In one embodiment, the proteins are expressed in a host cell such that the protein is glycosylated. In another embodiment, the proteins are expressed in a host cell such that the protein is aglycosylated.

In some embodiments, the cancer is any cancer that is sensitive to kynurenine depletion. In one embodiment, the present invention contemplates a method of treating a tumor cell or a cancer patient comprising administering a formulation comprising such a polypeptide. In some embodiments, the administration occurs under conditions such that at least a portion of the cells of the cancer are killed. In another embodiment, the formulation comprises such a kynureninase with kynurenine-degrading activity at physiological conditions and further comprising an attached polyethylene glycol chain. In some embodiment, the formulation is a pharmaceutical formulation comprising any of the above discussed kynureninases and pharmaceutically acceptable excipients. Such pharmaceutically acceptable excipients are well known to those of skill in the art. All of the above kynureninases may be contemplated as useful for human therapy.

In a further embodiment, there may also be provided a method of treating a tumor cell comprising administering a formulation comprising a non-bacterial (mammalian, e.g., primate or mouse) kynureninase that has kynurenine-degrading activity or a nucleic acid encoding thereof.

In accordance with certain aspects of the present invention, such a formulation containing the kynureninase can be administered intravenously, intradermally, intraarterially, intraperitoneally, intralesionally, intracranially, intraarticularly, intraprostaticaly, intrapleurally, intrasynovially, intratracheally, intranasally, intravitreally, intravaginally, intrarectally, intratumorally, intramuscularly, subcutaneously, subconjunctival, intravesicularlly, mucosally, intrapericardially, intraumbilically, intraocularly, orally, topically, by inhalation, infusion, continuous infusion, localized perfusion, via a catheter, via a lavage, in lipid compositions (e.g., liposomes), or by other method or any combination of the forgoing as would be known to one of ordinary skill in the art.

In a further embodiment, the method also comprises administering at least a second anticancer therapy to the subject. The second anticancer therapy may be a surgical therapy, chemotherapy, radiation therapy, cryotherapy, hormone therapy, immunotherapy or cytokine therapy. In certain aspects, the second anticancer therapy may be an antibody therapy such as anti-PD-1, anti-CTLA-4, anti-PD-L1 antibody, anti-LAG3, anti-TIM-3, anti-ICOS, anti-CD137, anti-CD40, anti-KIR, anti-CD40L, anti-GITR, or anti-OX40 therapy.

In some embodiments, a T cell comprising a chimeric antigen receptor (CAR) and a kynureninase enzyme are contemplated for use in treating a subject with cancer. In some aspects, the cell may be transfected with a DNA encoding the CAR and the kynureninase and, in some cases, a transposase.

The CAR may target any cancer-cell antigen of interest, including, for example, HER2, CD19, CD20, and GD2. The antigen binding regions or domain can comprise a fragment of the $V_H$ and $V_L$ chains of a single-chain variable fragment (scFv) derived from a particular human monoclonal antibody, such as those described in U.S. Pat. No. 7,109,304, which is incorporated herein by reference in its entirety. The fragment can also be any number of different antigen binding domains of a human antigen-specific antibody. In a more specific embodiment, the fragment is an antigen-specific scFv encoded by a sequence that is optimized for human codon usage for expression in human cells. For additional examples of CARs, see, for example, WO 2012/031744, WO 2012/079000, WO 2013/059593, and U.S. Pat. No. 8,465,743, all of which are incorporated herein by reference in their entireties.

The kynureninase may be any kynureninase disclosed herein. Methods of transfecting of cells are well known in the art, but in certain aspects, highly efficient transfections methods such as electroporation are employed. For example, nucleic acids may be introduced into cells using a nucleofection apparatus. Preferably, the transfection step does not involve infecting or transducing the cells with virus, which can cause genotoxicity and/or lead to an immune response to cells containing viral sequences in a treated subject.

A wide range of CAR constructs and expression vectors for the same are known in the art and are further detailed herein. For example, in some aspects, the CAR expression vector is a DNA expression vector such as a plasmid, linear expression vector or an episome. In some aspects, the vector comprises additional sequences, such as sequence that facilitates expression of the CAR, such a promoter, enhancer, poly-A signal, and/or one or more introns. In preferred aspects, the CAR coding sequence is flanked by transposon sequences, such that the presence of a transposase allows the coding sequence to integrate into the genome of the transfected cell.

In certain aspects, cells are further transfected with a transposase that facilitates integration of a CAR coding sequence into the genome of the transfected cells. In some aspects, the transposase is provided as DNA expression vector. However, in preferred aspects, the transposase is provided as an expressible RNA or a protein such that long-term expression of the transposase does not occur in the transgenic cells. Any transposase system may be used in accordance with the embodiments. In other aspects, cells may be infected with a lentivirus to facilitate integration of the CAR coding sequence and the kynureninase coding sequence into the genome of the cell.

In one embodiment, a composition comprising a kynureninase or a nucleic acid encoding a kynureninase is provided for use in the treatment of a tumor in a subject. In another embodiment, the use of a kynureninase or a nucleic acid encoding a kynureninase in the manufacture of a medicament for the treatment of a tumor is provided. Said kynureninase may be any kynureninase of the embodiments.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding," with reference to a nucleic acid, are used to make the invention readily understandable by the skilled artisan; however, these terms may be used interchangeably with "comprise" or "comprising," respectively.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
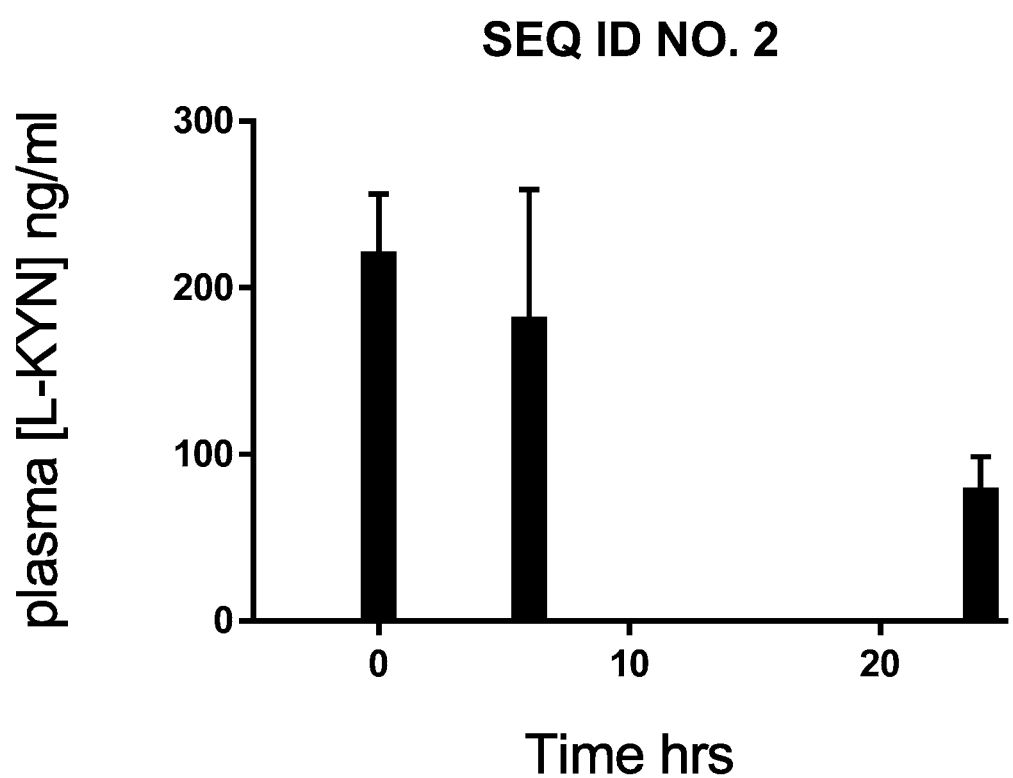
FIG. 1: Mice bearing CT26 tumors (n=4 each time point) were injected with 50 mg/kg PEGylated kynureninase (SEQ ID NO:2) by peri-tumoral injection at time=0 hours, and plasma KYN levels were assessed by mass spectrometry at 0, 6, and 24 hours.

Kynurenine (KYN) is a metabolite of the amino acid tryptophan generated via the action of either indolamine-2,3-dioxygenase (IDO) or tryptophan-2,3-dioxygenase (TDO). Kynurenine exerts multiple effects on cell physiology, one of the most important of which is modulation of T cell responses. Many tumor cells regulate the synthesis of IDO and/or TDO to elevate the local concentration of kynurenine, which is accompanied with depletion of tryptophan. High levels of kynurenine serve as a powerful way to inhibit the function of tumor infiltrating T cells that would otherwise attack the tumor.

The present invention provides methods for the use of kynurenine degrading enzymes as a means for depleting local kynurenine levels in the tumor microenvironment as well as in the serum and thus prevent tumor-mediated suppression of T-cell action. Kynurenine hydrolyzing enzymes (kynureninases) convert kynurenine to alanine and anthranilic acid, the latter of which is not known to affect T-cell function. The inventors generated a pharmaceutical preparation of kynureninase enzyme to enable the enzyme to persist for prolonged times under physiological conditions. The inventors then showed that intratumoral administration of the enzyme results in dramatic retardation of growth of an aggressive tumor in mice.

I. DEFINITIONS

As used herein the terms "protein" and "polypeptide" refer to compounds comprising amino acids joined via peptide bonds and are used interchangeably.

As used herein, the term "fusion protein" refers to a chimeric protein containing proteins or protein fragments operably linked in a non-native way.

As used herein, the term "half-life" (½-life) refers to the time that would be required for the concentration of a polypeptide thereof to fall by half in vitro or in vivo, for example, after injection in a mammal.

The terms "in operable combination," "in operable order," and "operably linked" refer to a linkage wherein the components so described are in a relationship permitting them to function in their intended manner, for example, a linkage of nucleic acid sequences in such a manner that a nucleic acid molecule capable of directing the transcription of a given gene and/or the synthesis of desired protein molecule, or a linkage of amino acid sequences in such a manner so that a fusion protein is produced.

The term "linker" is meant to refer to a compound or moiety that acts as a molecular bridge to operably link two different molecules, wherein one portion of the linker is operably linked to a first molecule, and wherein another portion of the linker is operably linked to a second molecule.

The term "PEGylated" refers to conjugation with polyethylene glycol (PEG), which has been widely used as a drug carrier, given its high degree of biocompatibility and ease of modification. PEG can be coupled (e.g., covalently linked) to active agents through the hydroxy groups at the end of the PEG chain via chemical methods; however, PEG itself is limited to at most two active agents per molecule. In a different approach, copolymers of PEG and amino acids have been explored as novel biomaterial that would retain the biocompatibility of PEG, but that would have the added advantage of numerous attachment points per molecule (thus providing greater drug loading), and that can be synthetically designed to suit a variety of applications.

The term "gene" refers to a DNA sequence that comprises control and coding sequences necessary for the production of a polypeptide or precursor thereof. The polypeptide can be encoded by a full-length coding sequence or by any portion of the coding sequence so as the desired enzymatic activity is retained.

The term "native" refers to the typical form of a gene, a gene product, or a characteristic of that gene or gene product when isolated from a naturally occurring source. A native form is that which is most frequently observed in a natural population and is thus arbitrarily designated the normal or wild-type form. In contrast, the term "modified," "variant," or "mutant" refers to a gene or gene product that displays modification in sequence and functional properties (i.e., altered characteristics) when compared to the native gene or gene product.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques The term "expression vector" refers to any type of genetic construct comprising a nucleic acid coding for an RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

The term "therapeutically effective amount" as used herein refers to an amount of cells and/or therapeutic composition (such as a therapeutic polynucleotide and/or therapeutic polypeptide) that is employed in methods to achieve a therapeutic effect. The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

The term "$K_M$" as used herein refers to the Michaelis-Menten constant for an enzyme and is defined as the concentration of the specific substrate at which a given enzyme yields one-half its maximum velocity in an enzyme catalyzed reaction. The term "$k_{cat}$" as used herein refers to the turnover number or the number of substrate molecules each enzyme site converts to product per unit time, and in which the enzyme is working at maximum efficiency. The term "$k_{cat}/K_M$" as used herein is the specificity constant, which is a measure of how efficiently an enzyme converts a substrate into product.

The term "chimeric antigen receptors (CARs)," as used herein, may refer to artificial T-cell receptors, chimeric T-cell receptors, or chimeric immunoreceptors, for example, and encompass engineered receptors that graft an artificial specificity onto a particular immune effector cell. CARs may be employed to impart the specificity of a monoclonal antibody onto a T cell, thereby allowing a large number of specific T cells to be generated, for example, for use in adoptive cell therapy. In specific embodiments, CARs direct specificity of the cell to a tumor associated antigen, for example. In some embodiments, CARs comprise an intracellular activation domain, a transmembrane domain, and an extracellular domain comprising a tumor associated antigen binding region. In particular aspects, CARs comprise fusions of single-chain variable fragments (scFv) derived from monoclonal antibodies (such as those described in U.S. Pat. No. 7,109,304, which is incorporated herein by reference in its entirety), fused to CD3-zeta transmembrane and endodomains. The specificity of other CAR designs may be derived from ligands of receptors (e.g., peptides) or from pattern-recognition receptors, such as Dectins. In particular embodiments, one can target malignant B cells by redirecting the specificity of T cells by using a CAR specific for the B-lineage molecule, CD19. In certain cases, the spacing of the antigen-recognition domain can be modified to reduce activation-induced cell death. In certain cases, CARs comprise domains for additional co-stimulatory signaling, such as CD3-zeta, FcR, CD27, CD28, CD137, DAP10, and/or OX40. In some cases, molecules can be co-expressed with the CAR, including co-stimulatory molecules, reporter genes for imaging (e.g., for positron emission tomography), gene products that conditionally ablate the T cells upon addition of a pro-drug, homing receptors, chemokines, chemokine receptors, cytokines, and cytokine receptors.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of a kynureninase.

"Subject" and "patient" refer to either a human or non-human, such as primates, mammals, and vertebrates. In particular embodiments, the subject is a human.

II. KYNURENINASE POLYPEPTIDES

Some embodiments concern modified proteins and polypeptides. Particular embodiments concern a modified protein or polypeptide that exhibits at least one functional activity that is comparable to the unmodified version, preferably, the kynurenine degrading activity. In further aspects, the protein or polypeptide may be further modified to increase serum stability. Thus, when the present application refers to the function or activity of "modified protein" or a "modified polypeptide," one of ordinary skill in the art would understand that this includes, for example, a protein or polypeptide that possesses an additional advantage over the unmodified protein or polypeptide, such as kynurenine degrading activity or thermodynamic stability.

Determination of activity may be achieved using assays familiar to those of skill in the art, particularly with respect to the protein's activity, and may include for comparison purposes, the use of native and/or recombinant versions of either the modified or unmodified protein or polypeptide.

In certain embodiments, a modified polypeptide, such as a modified kynureninase, may be identified based on its increase in kynurenine. For example, substrate recognition sites of the unmodified polypeptide may be identified. This identification may be based on structural analysis or homology analysis. A population of mutants involving modifications of such substrate recognition sites may be generated. In a further embodiment, mutants with increased kynurenine degrading activity may be selected from the mutant population. Selection of desired mutants may include methods, such as detection of byproducts or products from kynurenine degradation.

Modified proteins may possess deletions and/or substitutions of amino acids; thus, a protein with a deletion, a protein with a substitution, and a protein with a deletion and a substitution are modified proteins. In some embodiments, these modified proteins may further include insertions or added amino acids, such as with fusion proteins or proteins with linkers, for example. A "modified deleted protein" lacks one or more residues of the native protein, but may possess the specificity and/or activity of the native protein. A "modified deleted protein" may also have reduced immunogenicity or antigenicity. An example of a modified deleted protein is one that has an amino acid residue deleted from at least one antigenic region that is, a region of the protein determined to be antigenic in a particular organism, such as the type of organism that may be administered the modified protein.

Substitution or replacement variants typically contain the exchange of one amino acid for another at one or more sites within the protein and may be designed to modulate one or more properties of the polypeptide, particularly its effector functions and/or bioavailability. Substitutions may or may not be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine, or methionine; serine to threonine; threonine to serine; tryptophan to tyrosine; tyrosine to tryptophan or phenylalanine; and valine to isoleucine or leucine.

In addition to a deletion or substitution, a modified protein may possess an insertion of residues, which typically involves the addition of at least one residue in the polypeptide. This may include the insertion of a targeting peptide or polypeptide or simply a single residue. Terminal additions, called fusion proteins, are discussed below.

The term "biologically functional equivalent" is well understood in the art and is further defined in detail herein. Accordingly, sequences that have between about 70% and about 80%, or between about 81% and about 90%, or even between about 91% and about 99% of amino acids that are identical or functionally equivalent to the amino acids of a control polypeptide are included, provided the biological activity of the protein is maintained. A modified protein may be biologically functionally equivalent to its native counterpart in certain aspects.

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

III. ENZYMATIC KYNURENINE DEGRADATION FOR THERAPY

In certain aspects, the polypeptides may be used for the treatment of diseases, including cancers that are sensitive to kynurenine depletion, with enzymes that deplete kynurenine, to prevent tumor-mediated tolerogenic effects and instead mediate tumor-ablating pro-inflammatory responses. In certain aspects, kynureninases are contemplated for use in treating tumors expressing IDO1, IDO2, and/or TDO.

Certain aspects of the present invention provide a modified kynureninase for treating diseases, such as tumors. Particularly, the modified polypeptide may have human polypeptide sequences and thus may prevent allergic reactions in human patients, allow repeated dosing, and increase the therapeutic efficacy.

Tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, carcinoma, lymphoma, blastoma, sarcoma, leukemia, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer and gastrointestinal stromal cancer), pancreatic cancer, glioblastoma, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, melanoma, superficial spreading melanoma, lentigo malignant melanoma, acral lentiginous melanomas, nodular melanomas, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's macroglobulinemia), chronic lymphocytic leukemia (CLL), acute lymphoblastic leukemia (ALL), Hairy cell leukemia, multiple myeloma, acute myeloid leukemia (AML) and chronic myeloblastic leukemia.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The kynureninase may be used herein as an antitumor agent in a variety of modalities for depleting kynurenine and/or kynurenine-derived metabolites from tumor tissue, or the circulation of a mammal with cancer, or for depletion of kynurenine where its depletion is considered desirable.

Depletion can be conducted in vivo in the circulation of a mammal, in vitro in cases where kynurenine and/or kynurenine-derived metabolites depletion in tissue culture or other biological mediums is desired, and in ex vivo procedures where biological fluids, cells, or tissues are manipulated outside the body and subsequently returned to the body of the patient mammal. Depletion of kynurenine from circulation, culture media, biological fluids, or cells is conducted to reduce the amount of kynurenine accessible to the material being treated, and therefore comprises contacting the material to be depleted with a kynurenine-depleting amount of the kynureninase under kynurenine-depleting conditions as to degrade the ambient kynurenine in the material being contacted.

The depletion may be directed to the nutrient source for the cells, and not necessarily the cells themselves. Therefore, in an in vivo application, treating a tumor cell includes contacting the nutrient medium for a population of tumor cells with the kynureninase. In this embodiment, the medium may be blood, lymphatic fluid, spinal fluid and the like bodily fluid where kynurenine depletion is desired.

Kynurenine- and/or kynurenine-derived metabolites depletion efficiency can vary widely depending upon the application, and typically depends upon the amount of kynurenine present in the material, the desired rate of depletion, and the tolerance of the material for exposure to kynureninase. Kynurenine and kynurenine metabolite levels in a material, and therefore rates of kynurenine and kynurenine metabolite depletion from the material, can readily be monitored by a variety of chemical and biochemical methods well known in the art. Exemplary kynurenine-depleting amounts are described further herein, and can range from 0.001 to 100 units (U) of kynureninase, preferably about 0.01 to 10 U, and more preferably about 0.1 to 5 U kyureninase per milliliter (mL) of material to be treated. Typical dosages can be administered based on body weight, and are in the range of about 5-1000 U/kilogram (kg)/day, preferably about 5-100 U/kg/day, more preferably about 10-50 U/kg/day, and more preferably about 20-40 U/kg/day.

Kynurenine-depleting conditions are buffer and temperature conditions compatible with the biological activity of a kynureninase, and include moderate temperature, salt, and pH conditions compatible with the enzyme, for example, physiological conditions. Exemplary conditions include about 4-40° C., ionic strength equivalent to about 0.05 to 0.2 M NaCl, and a pH of about 5 to 9, while physiological conditions are included.

In a particular embodiment, the invention contemplates methods of using a kynureninase as an antitumor agent, and therefore comprises contacting a population of tumor cells with a therapeutically effective amount of kynureninase for a time period sufficient to inhibit tumor cell growth.

A therapeutically effective amount of a kynureninase is a predetermined amount calculated to achieve the desired effect, i.e., to deplete kynurenine in the tumor tissue or in a patient's circulation, and thereby mediate a tumor-ablating pro-inflammatory response. Thus, the dosage ranges for the administration of kynureninase of the invention are those large enough to produce the desired effect in which the symptoms of tumor cell division and cell cycling are reduced. The dosage should not be so large as to cause adverse side effects, such as hyperviscosity syndromes, pulmonary edema, congestive heart failure, neurological effects, and the like. Generally, the dosage will vary with age of, condition of, sex of, and extent of the disease in the patient and can be determined by one of skill in the art. The dosage can be adjusted by the individual physician in the event of any complication.

The kynureninase can be administered parenterally by injection or by gradual infusion over time. The kynureninase can be administered intravenously, intraperitoneally, orally, intramuscularly, subcutaneously, intracavity, transdermally, dermally, can be delivered by peristaltic means, can be injected directly into the tissue containing the tumor cells, or can be administered by a pump connected to a catheter that may contain a potential biosensor for kynurenine.

The therapeutic compositions containing kynureninase are conventionally administered intravenously, as by injection of a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required diluent, i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for initial administration and booster shots are also contemplated and are typified by an initial administration followed by repeated doses at one or more hour intervals by a subsequent injection or other administration. Exemplary multiple administrations are described herein and are particularly preferred to maintain continuously high serum and tissue levels of kynureninase and conversely low serum and tissue levels of kynurenine. Alternatively, continuous intravenous infusion sufficient to maintain concentrations in the blood in the ranges specified for in vivo therapies are contemplated.

IV. CONJUGATES

Compositions and methods of the present invention involve modified kynureninases, such as by forming conjugates with heterologous peptide segments or polymers, such as polyethylene glycol. In further aspects, the kynureninases may be linked to PEG to increase the hydrodynamic radius of the enzyme and hence increase the serum persistence. In certain aspects, the disclosed polypeptide may be conjugated to any targeting agent, such as a ligand having the ability to specifically and stably bind to an external receptor or binding site on a tumor cell (U.S. Patent Publ. 2009/0304666).

A. Fusion Proteins

Certain embodiments of the present invention concern fusion proteins. These molecules may have a native or modified kynureninase linked at the N- or C-terminus to a heterologous domain. For example, fusions may also employ leader sequences from other species to permit the recombinant expression of a protein in a heterologous host. Another useful fusion includes the addition of a protein affinity tag, such as a serum albumin affinity tag or six histidine residues, or an immunologically active domain, such as an antibody epitope, preferably cleavable, to facilitate purification of the fusion protein. Non-limiting affinity tags include polyhistidine, chitin binding protein (CBP), maltose binding protein (MBP), and glutathione-S-transferase (GST).

In a particular embodiment, the kynureninase may be linked to a peptide that increases the in vivo half-life, such as an XTEN polypeptide (Schellenberger et al., 2009), IgG Fc domain, albumin, or albumin binding peptide.

Methods of generating fusion proteins are well known to those of skill in the art. Such proteins can be produced, for example, by de novo synthesis of the complete fusion protein, or by attachment of the DNA sequence encoding the heterologous domain, followed by expression of the intact fusion protein.

Production of fusion proteins that recover the functional activities of the parent proteins may be facilitated by connecting genes with a bridging DNA segment encoding a peptide linker that is spliced between the polypeptides connected in tandem. The linker would be of sufficient length to allow proper folding of the resulting fusion protein.

B. PEGylation

In certain aspects of the invention, methods and compositions related to PEGylation of kynureninase are disclosed. For example, the kynureninase may be PEGylated in accordance with the methods disclosed herein.

PEGylation is the process of covalent attachment of poly(ethylene glycol) polymer chains to another molecule, normally a drug or therapeutic protein. PEGylation is routinely achieved by incubation of a reactive derivative of PEG with the target macromolecule. The covalent attachment of PEG to a drug or therapeutic protein can "mask" the agent from the host's immune system (reduced immunogenicity and antigenicity) or increase the hydrodynamic size (size in solution) of the agent, which prolongs its circulatory time by reducing renal clearance. PEGylation can also provide water solubility to hydrophobic drugs and proteins.

The first step of the PEGylation is the suitable functionalization of the PEG polymer at one or both terminals. PEGs that are activated at each terminus with the same reactive moiety are known as "homobifunctional," whereas if the functional groups present are different, then the PEG derivative is referred as "heterobifunctional" or "heterofunctional." The chemically active or activated derivatives of the PEG polymer are prepared to attach the PEG to the desired molecule.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, and tyrosine. The N-terminal amino group and the C-terminal carboxylic acid can also be used.

The techniques used to form first generation PEG derivatives are generally reacting the PEG polymer with a group that is reactive with hydroxyl groups, typically anhydrides, acid chlorides, chloroformates, and carbonates. In the second generation PEGylation chemistry more efficient functional groups, such as aldehyde, esters, amides, etc., are made available for conjugation.

As applications of PEGylation have become more and more advanced and sophisticated, there has been an increase in need for heterobifunctional PEGs for conjugation. These heterobifunctional PEGs are very useful in linking two entities, where a hydrophilic, flexible, and biocompatible spacer is needed. Preferred end groups for heterobifunctional PEGs are maleimide, vinyl sulfones, pyridyl disulfide, amine, carboxylic acids, and NHS esters.

The most common modification agents, or linkers, are based on methoxy PEG (mPEG) molecules. Their activity depends on adding a protein-modifying group to the alcohol end. In some instances polyethylene glycol (PEG diol) is used as the precursor molecule. The diol is subsequently modified at both ends in order to make a hetero- or homo-dimeric PEG-linked molecule.

Proteins are generally PEGylated at nucleophilic sites, such as unprotonated thiols (cysteinyl residues) or amino groups. Examples of cysteinyl-specific modification reagents include PEG maleimide, PEG iodoacetate, PEG thiols, and PEG vinylsulfone. All four are strongly cysteinyl-specific under mild conditions and neutral to slightly alkaline pH but each has some drawbacks. The thioether formed with the maleimides can be somewhat unstable under alkaline conditions so there may be some limitation to formulation options with this linker. The carbamothioate linkage formed with iodo PEGs is more stable, but free iodine can modify tyrosine residues under some conditions. PEG thiols form disulfide bonds with protein thiols, but this linkage can also be unstable under alkaline conditions. PEG-vinylsulfone reactivity is relatively slow compared to maleimide and iodo PEG; however, the thioether linkage formed is quite stable. Its slower reaction rate also can make the PEG-vinylsulfone reaction easier to control.

Site-specific PEGylation at native cysteinyl residues is seldom carried out, since these residues are usually in the form of disulfide bonds or are required for biological activity. On the other hand, site-directed mutagenesis can be used to incorporate cysteinyl PEGylation sites for thiol-specific linkers. The cysteine mutation must be designed such that it is accessible to the PEGylation reagent and is still biologically active after PEGylation.

Amine-specific modification agents include PEG NHS ester, PEG tresylate, PEG aldehyde, PEG isothiocyanate, and several others. All react under mild conditions and are very specific for amino groups. The PEG NHS ester is probably one of the more reactive agents; however, its high reactivity can make the PEGylation reaction difficult to control on a large scale. PEG aldehyde forms an imine with the amino group, which is then reduced to a secondary amine with sodium cyanoborohydride. Unlike sodium borohydride, sodium cyanoborohydride will not reduce disulfide bonds. However, this chemical is highly toxic and must be handled cautiously, particularly at lower pH where it becomes volatile.

Due to the multiple lysine residues on most proteins, site-specific PEGylation can be a challenge. Fortunately, because these reagents react with unprotonated amino groups, it is possible to direct the PEGylation to lower-pK amino groups by performing the reaction at a lower pH. Generally the pK of the alpha-amino group is 1-2 pH units lower than the epsilon-amino group of lysine residues. By PEGylating the molecule at pH 7 or below, high selectivity for the N-terminus frequently can be attained. However, this is only feasible if the N-terminal portion of the protein is not required for biological activity. Still, the pharmacokinetic benefits from PEGylation frequently outweigh a significant loss of in vitro bioactivity, resulting in a product with much greater in vivo bioactivity regardless of PEGylation chemistry.

There are several parameters to consider when developing a PEGylation procedure. Fortunately, there are usually no more than four or five key parameters. The "design of experiments" approach to optimization of PEGylation conditions can be very useful. For thiol-specific PEGylation reactions, parameters to consider include: protein concentration, PEG-to-protein ratio (on a molar basis), temperature, pH, reaction time, and in some instances, the exclusion of oxygen. (Oxygen can contribute to intermolecular disulfide formation by the protein, which will reduce the yield of the PEGylated product.) The same factors should be considered (with the exception of oxygen) for amine-specific modification except that pH may be even more critical, particularly when targeting the N-terminal amino group.

For both amine- and thiol-specific modifications, the reaction conditions may affect the stability of the protein. This may limit the temperature, protein concentration, and pH. In addition, the reactivity of the PEG linker should be known before starting the PEGylation reaction. For example, if the PEGylation agent is only 70 percent active, the amount of PEG used should ensure that only active PEG molecules are counted in the protein-to-PEG reaction stoichiometry.

V. PROTEINS AND PEPTIDES

In certain embodiments, the present invention concerns novel compositions comprising at least one protein or peptide, such as a kynureninase. These peptides may be comprised in a fusion protein or conjugated to an agent as described supra.

As used herein, a protein or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide," and "peptide" are used interchangeably herein.

As used herein, an "amino acid residue" refers to any naturally occurring amino acid, any amino acid derivative, or any amino acid mimic known in the art. In certain embodiments, the residues of the protein or peptide are sequential, without any non-amino acids interrupting the sequence of amino acid residues. In other embodiments, the sequence may comprise one or more non-amino acid moieties. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid.

Proteins or peptides may be made by any technique known to those of skill in the art, including the expression of proteins, polypeptides, or peptides through standard molecular biological techniques, the isolation of proteins or peptides from natural sources, or the chemical synthesis of proteins or peptides. The nucleotide and protein, polypeptide, and peptide sequences corresponding to various genes have been previously disclosed, and may be found at computerized databases known to those of ordinary skill in the art. One such database is the National Center for Biotechnology Information's Genbank and GenPept databases (available on the world wide web at ncbi.nlm.nih.gov/). The coding regions for known genes may be amplified and/or expressed using the techniques disclosed herein or as would be known to those of ordinary skill in the art. Alternatively, various commercial preparations of proteins, polypeptides, and peptides are known to those of skill in the art.

VI. NUCLEIC ACIDS AND VECTORS

In certain aspects of the invention, nucleic acid sequences encoding a kynureninase or a fusion protein containing a kynureninase may be disclosed. Depending on which expression system is used, nucleic acid sequences can be selected based on conventional methods. For example, if the kynureninase is derived from human kynureninase and contains multiple codons that are rarely utilized in *E. coli*, then that may interfere with expression. Therefore, the respective genes or variants thereof may be codon optimized for *E. coli* expression. Various vectors may be also used to express the protein of interest. Exemplary vectors include, but are not limited, plasmid vectors, viral vectors, transposon, or liposome-based vectors.

VII. HOST CELLS

Host cells may be any that may be transformed to allow the expression and secretion of kynureninase and conjugates thereof. The host cells may be bacteria, mammalian cells, yeast, or filamentous fungi. Various bacteria include *Escherichia* and *Bacillus*. Yeasts belonging to the genera *Saccharomyces*, or *Pichia* would find use as an appropriate

VIII. PHARMACEUTICAL COMPOSITIONS

It is contemplated that the novel kynureninase can be administered systemically or locally to inhibit tumor cell growth and, most preferably, to kill cancer cells in cancer patients with locally advanced or metastatic cancers. They can be administered intravenously, intrathecally, and/or intraperitoneally. They can be administered alone or in combination with anti-proliferative drugs. In one embodiment, they are administered to reduce the cancer load in the patient prior to surgery or other procedures. Alternatively, they can be administered after surgery to ensure that any remaining cancer (e.g., cancer that the surgery failed to eliminate) does not survive.

It is not intended that the present invention be limited by the particular nature of the therapeutic preparation. For example, such compositions can be provided in formulations together with physiologically tolerable liquid, gel, or solid carriers, diluents, and excipients. These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual subjects.

Such compositions are typically prepared as liquid solutions or suspensions, as injectables. Suitable diluents and excipients are, for example, water, saline, dextrose, glycerol, or the like, and combinations thereof. In addition, if desired, the compositions may contain minor amounts of auxiliary substances, such as wetting or emulsifying agents, stabilizing agents, or pH buffering agents.

Where clinical applications are contemplated, it may be necessary to prepare pharmaceutical compositions comprising proteins, antibodies, and drugs in a form appropriate for the intended application. Generally, pharmaceutical compositions may comprise an effective amount of one or more kynureninase or additional agents dissolved or dispersed in a pharmaceutically acceptable carrier. The phrases "pharmaceutical or pharmacologically acceptable" refers to molecular entities and compositions that do not produce an adverse, allergic, or other untoward reaction when administered to an animal, such as, for example, a human, as appropriate. The preparation of a pharmaceutical composition that contains at least one kyureninase isolated by the method disclosed herein, or additional active ingredient will be known to those of skill in the art in light of the present disclosure, as exemplified by Remington's Pharmaceutical Sciences, 18th Ed., 1990, incorporated herein by reference. Moreover, for animal (e.g., human) administration, it will be understood that preparations should meet sterility, pyrogenicity, general safety, and purity standards as required by the FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed., 1990, incorporated herein by reference). Except insofar as any conventional carrier is incompatible with the active ingredient, its use in the pharmaceutical compositions is contemplated.

Certain embodiments of the present invention may comprise different types of carriers depending on whether it is to be administered in solid, liquid, or aerosol form, and whether it needs to be sterile for the route of administration, such as injection. The compositions can be administered intravenously, intradermally, transdermally, intrathecally, intraarterially, intraperitoneally, intranasally, intravaginally, intrarectally, intramuscularly, subcutaneously, mucosally, orally, topically, locally, by inhalation (e.g., aerosol inhalation), by injection, by infusion, by continuous infusion, by localized perfusion bathing target cells directly, via a catheter, via a lavage, in lipid compositions (e.g., liposomes), or by other methods or any combination of the forgoing as would be known to one of ordinary skill in the art (see, for example, Remington's Pharmaceutical Sciences, 18th Ed., 1990, incorporated herein by reference).

The modified polypeptides may be formulated into a composition in a free base, neutral, or salt form. Pharmaceutically acceptable salts include the acid addition salts, e.g., those formed with the free amino groups of a proteinaceous composition, or which are formed with inorganic acids, such as, for example, hydrochloric or phosphoric acids, or such organic acids as acetic, oxalic, tartaric, or mandelic acid. Salts formed with the free carboxyl groups can also be derived from inorganic bases, such as, for example, sodium, potassium, ammonium, calcium, or ferric hydroxides; or such organic bases as isopropylamine, trimethylamine, histidine, or procaine. Upon formulation, solutions will be administered in a manner compatible with the dosage formulation and in such amount as is therapeutically effective. The formulations are easily administered in a variety of dosage forms, such as formulated for parenteral administrations, such as injectable solutions, or aerosols for delivery to the lungs, or formulated for alimentary administrations, such as drug release capsules and the like.

Further in accordance with certain aspects of the present invention, the composition suitable for administration may be provided in a pharmaceutically acceptable carrier with or without an inert diluent. The carrier should be assimilable and includes liquid, semi-solid, i.e., pastes, or solid carriers. Except insofar as any conventional media, agent, diluent, or carrier is detrimental to the recipient or to the therapeutic effectiveness of the composition contained therein, its use in administrable composition for use in practicing the methods is appropriate. Examples of carriers or diluents include fats, oils, water, saline solutions, lipids, liposomes, resins, binders, fillers, and the like, or combinations thereof. The composition may also comprise various antioxidants to retard oxidation of one or more component. Additionally, the prevention of the action of microorganisms can be brought about by preservatives, such as various antibacterial and antifungal agents, including but not limited to parabens (e.g., methylparabens, propylparabens), chlorobutanol, phenol, sorbic acid, thimerosal or combinations thereof.

In accordance with certain aspects of the present invention, the composition is combined with the carrier in any convenient and practical manner, i.e., by solution, suspension, emulsification, admixture, encapsulation, absorption, and the like. Such procedures are routine for those skilled in the art.

In a specific embodiment of the present invention, the composition is combined or mixed thoroughly with a semi-solid or solid carrier. The mixing can be carried out in any convenient manner, such as grinding. Stabilizing agents can be also added in the mixing process in order to protect the composition from loss of therapeutic activity, i.e., denaturation in the stomach. Examples of stabilizers for use in a composition include buffers, amino acids, such as glycine and lysine, carbohydrates, such as dextrose, mannose, galactose, fructose, lactose, sucrose, maltose, sorbitol, mannitol, etc.

In further embodiments, the present invention may concern the use of a pharmaceutical lipid vehicle composition that includes kynureninases, one or more lipids, and an aqueous solvent. As used herein, the term "lipid" will be defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds that contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether- and ester-linked fatty acids, polymerizable lipids, and combinations thereof. Of course, compounds other than those specifically described herein that are understood by one of skill in the art as lipids are also encompassed by the compositions and methods.

One of ordinary skill in the art would be familiar with the range of techniques that can be employed for dispersing a composition in a lipid vehicle. For example, the kynureninase or a fusion protein thereof may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition administered to an animal patient can be determined by physical and physiological factors, such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared in such a way that a suitable dosage will be obtained in any given unit dose of the compound. Factors, such as solubility, bioavailability, biological half-life, route of administration, product shelf life, as well as other pharmacological considerations, will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 milligram/kg/body weight or more per administration, and any range derivable therein. In non-limiting examples of a derivable range from the numbers listed herein, a range of about 5 milligram/kg/body weight to about 100 milligram/kg/body weight, about 5 microgram/kg/body weight to about 500 milligram/kg/body weight, etc., can be administered, based on the numbers described above.

IX. COMBINATION TREATMENTS

In certain embodiments, the compositions and methods of the present embodiments involve administration of a kynureninase in combination with a second or additional therapy. Such therapy can be applied in the treatment of any disease that is associated with kynurenine dependency. For example, the disease may be cancer.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve administering a kynureninase and a second therapy. The second therapy may or may not have a direct cytotoxic effect. For example, the second therapy may be an agent that upregulates the immune system without having a direct cytotoxic effect. A tissue, tumor, or cell can be exposed to one or more compositions or pharmacological formulation(s) comprising one or more of the agents (e.g., a kynureninase or an anti-cancer agent), or by exposing the tissue, tumor, and/or cell with two or more distinct compositions or formulations, wherein one composition provides 1) a kynureninase, 2) an anti-cancer agent, or 3) both a kynureninase and an anti-cancer agent. Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

A kynureninase may be administered before, during, after, or in various combinations relative to an anti-cancer treatment. The administrations may be in intervals ranging from concurrently to minutes to days to weeks. In embodiments where the kynureninase is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the kynureninase and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below a kynureninase is "A" and an anti-cancer therapy is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

X. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Gene Construction, Expression, and Purification of Kynureninase from *Homo sapiens*

A gene for expression of the kynureninase enzyme from *Homo sapiens* (h-KYNU) was obtained by overlap extension polymerase chain reaction (PCR) of four codon optimized gene blocks designed using DNA-Works software (Hoover and Lubkowski, 2002). The full-length gene includes an N-terminal XbaI restriction enzyme site (nucleotides 1-6), an optimized ribosomal binding site (nucleotides 28-60), a start codon (nucleotides 61-63), an N-terminal His$_6$ tag (nucleotides 64-96), an *E. coli* codon optimized h-KYNU gene (nucleotides 97-1488), a stop codon (nucleotides 1489-1491), and a C-terminal BamHI restriction enzyme site (nucleotides 1492-1497) (SEQ ID NO: 34). The aforementioned restriction enzyme sites were used to clone the assembled gene into a pET-28a+ vector (Novagen). This construct was then used to transform BL21 (DE3) *E. coli* for expression. Cells were grown at 37° C. with shaking at 210 rpm in Terrific Broth (TB) media with 50 mg/L of kanamycin. Expression was induced when an OD$_{600}$ ~1.0 was reached by adding IPTG (0.5 mM final concentration) with continued shaking overnight at 25° C. Cells were then harvested by centrifugation and re-suspended in lysis buffer consisting of 100 mM sodium phosphate, pH 8.0, 300 mM NaCl, 25 mM imidazole, 1 mM pyridoxyl phosphate (PLP), 1 mM phenylmethylsulfonylfluoride, 0.1% Tween 20, and 25 U/mL Pierce™ Universal Nuclease for Cell Lysis (ThermoFisher Scientific). Lysis was achieved by French press and the lysate was cleared of particulates by centrifuging at 20,000×g for 1 h at 25° C. The supernatant was then filtered through a 0.45 μm syringe filter and applied to a Ni-NTA/agarose column (Qiagen) pre-equilibrated in 100 mM sodium phosphate, pH 8.0, 300 mM NaCl, 25 mM imidazole, and 0.1% Tween 20.

After loading the lysate onto the column, the resin was washed with 20 column volumes (CV) of 100 mM sodium phosphate, pH 8.0, 300 mM NaCl, 25 mM imidazole, and 0.1% Tween 20. The enzyme was then eluted in 5 CV of 300 mM NaCl, 100 mM sodium phosphate pH 8.0, 10 mM PLP and 300 mM imidazole, and then incubated at 37° C. for two hours in the elution buffer to ensure proper PLP loading. At this point, enzyme was dialyzed against 4L of 50 mM Tris-HCl pH 8.5 overnight at 4° C. to remove excess PLP and imidazole, and 10% glycerol was added to the enzyme and aliquots were flash frozen in liquid nitrogen for storage at −80° C. Alternatively, enzyme could be buffer exchanged into freshly made, sterile 100 mM sodium phosphate, pH 8.4, to both remove imidazole and PLP and prepare it for PEGylation (see Example 4 of PCT/US2014/053437). Enzyme purities were typically >95% as assessed by SDS-PAGE analysis and typical yields averaged around 5 mg/L of liquid culture. Protein quantities were assessed by measuring $Abs_{280\ nm}$.

Example 2—Assay for Measuring Kinetic Parameters of Kynureninase

The kinetic parameters of h-KYNU, and of h-KYNU variants as described in Examples 5, 6, and 7 below, were quantified by a spectrophotometric assay, in which the decay in the maximum absorbance of the enzyme substrate, L-kynurenine, was monitored as a function of time. L-kynurenine solutions were prepared in a PBS buffer, pH 7.4, to result in final concentrations ranging from 31 µM to 2000 µM. L-Kynurenine has an extinction coefficient of 4,500 $M^{-1}cm^{-1}$ with a $\lambda_{max}$ at 365 nm while the products of the kynureninase reaction, L-anthranilic acid and L-alanine, do not appreciably absorb at 365 nm. Reactions were initiated by adding and rapidly mixing enzyme solutions (~20 nM final) with the substrate solutions and monitoring the loss of substrate KYN at 37° C. by measuring $Abs_{365\ nm}$ over time. The resulting data was processed and fitted to the Michaelis-Menten equation for determining kinetic constants. For the authentic (wild-type) h-KYNU enzyme, $k_{cat}/K_M=1.0\times10^2\ M^{-1}s^{-1}$.

Example 3—Genetic Selection for Kynureninase Activity

The amino acid L-tryptophan (L-Trp) is synthesized from the pentose derived precursor, chorismate, by expression of the trp biosynthetic genes. In bacteria such as *E. coli* the trp biosynthetic genes are organized in an operon composed of five genes; trpE, trpD, trpC, trpB, and trpA. The TrpE and TrpD proteins are components of the anthranilate synthase complex that catalyzes the first step in the conversion of chorismate and L-glutamine to anthranilic acid and L-glutamate. Anthranilic acid is then subsequently converted to L-Trp by the action of TrpD, TrpC, TrpA, and TrpB. Cells lacking a functional anthranilate synthase gene are auxotrophic for L-Trp and cannot grow in minimal media without tryptophan. The inventors postulated that since kynurenine can be transported into the cytosol of many organisms, cells expressing recombinant L-kynureninase (h-KYNase) enzymes displaying a sufficiently high catalytic activity should be able to convert cytosolic L-kynurenine to anthranilic acid and the latter then enables the synthesis of L-Trp. By contrast, cells that do not express the enzyme or express variants with low catalytic activity should display either no growth or very slow growth, respectively, on minimal media with L-kynurenine.

To select h-KYNase bacteria transformed with library DNA expressing h-KYNase enzyme variants were grown in culture media, dubbed M9-KYN media, contained M9 minimal salts, 2 mM magnesium sulfate, 0.1 mM calcium chloride, 2% glucose, 10 µM IPTG, ampicillin, 100 µM Kynurenine, and water. As described above, an *E. coli* ΔtrpE deletion mutant was utilized for genetic selection experiments. The *E. coli* ΔtrpE strain was obtained from Genetic Resources at Yale CGSC and had the genotype (F-, Δ(araD-araB)567, ΔlacZ4787(::rmB-3), λ⁻, ΔtrpE772::kan, rph-1, Δ(rhaD-rhaB)568, hsdR514). Clones expressing enzymes having better catalytic activity for KYN degradation and/or expression are able to grow better in the M9-KYN media and thus become enriched.

Example 4—Construction of an *E. coli* Tac Promoter Expression Vector with Chloramphenicol Resistance for Use in Genetic Selections (See Example 3 Above)

In total, six nucleotide fragments were PCR amplified for downstream Gibson-mediated assembly (see Gibson et al, "Enzymatic Assembly of DNA molecules up to several hundred kilobases," Nature Methods 6:343-345 (2009), incorporated by reference). Four nucleotide fragments were PCR amplified using the *E. coli* expression vector pMAL-c2x as template and oligonucleotide primer pairs as follows: Pair 1=5' TAAACAACTGGCGGTATGGCCGACACCAT-CGAATGGTGC 3' (SEQ ID NO: 10) and 5' GTTTTAT-CAATGCATTAGGTACCACTTGTTGGTGAAGTGC-TCGTGAAAAC 3' (SEQ ID NO: 11), Pair 2=5' GTGTATACTGGCTTAACTGGCCAGGAACCGTAAAA-AGGCC 3' (SEQ ID NO: 12) and 5' ATAGGCC-GAAATCGGCAAAAGGATCTAGGTGAAGATCCTTT-TTGATAATCTC 3' (SEQ ID NO: 13), Pair 3=5' CTTTT-TACGGTTCCTGGCCAGTTAAGCCAGTATACACTCC-GCTATCGC 3' (SEQ ID NO: 14) and 5' ACCATTC-GATGGTGTCGGCCATACCGCCAGTTGTTTACCCTC 3' (SEQ ID NO: 15), Pair 4=5' TGCCGCGGAT-TACCCGGGCTGCAGGCAAGCTTGGCACT 3' (SEQ ID NO: 16) and 5' CACCTGAAATTGTAAACGT-TAAAAAGGCCATCCGTCAGGATG 3' (SEQ ID NO: 17). The fifth nucleotide fragment containing the chloramphenicol resistance gene was PCR amplified using the *E. coli* phage display vector pAK200 as template and the following oligonucleotide primer pair: 5' CTGACGGATGGCCTTTT-TAACGTTTACAATTTCAGGTGGCACTTTTC 3' (SEQ ID NO: 18) and 5' GATCTTCACCTAGATCCTTTTAATT-ATTACCTCCACGGGGAGAGCC 3' (SEQ ID NO: 19). The sixth and final nucleotide fragment containing a partial sequence of the wildtype h-KYNU gene was amplified using the following oligonucleotide primer pair: 5' GTGGTAC-CTAATGCATTGATAAAACCGCGCGAAGGTG 3' (SEQ ID NO: 20) and 5' AGCCCGGGTAATCC-GCGGCAGCACGCAAAATCAACGCC 3' (SEQ ID NO: 21). These six fragments were assembled using Gibson-mediated assembly, resulting in an *E. coli* expression vector with chloramphenicol resistance that utilized the Tac promoter for expression of wildtype h-KYNU gene contained between XmaI and KpnI restriction enzyme sites (SEQ ID NO: 9).

Example 5—Isolation of h-KYNase Variants with Highly Enhanced Kynureninase Activity from Libraries of Random Mutants To engineer improved L-Kynurenine degrading activity into an h-KYNase variant with the mutations A99I/G112A/

F306Y/I405L/S408N/A436T (see SEQ ID NO: 93 of PCT/US2015/047475, incorporated herein as SEQ ID NO: 22), random mutations were introduced in SEQ ID NO: 22 by error-prone PCR of the entire gene for 25 cycles using Taq Polymerase and 0.22 mM dATP, 0.20 mM dCTP, 0.27 mM dGTP, 1.88 mM dTTP, 2.75 mM $MgCl_2$, 0.5 mM $MnCl_2$, 0.005 mg/ml BSA, and 0.5 mM of each primer of the following two primers: 5' CACTGTGTGGT-ACCGAGGTAATACATGGGCGGTCATCATCACCAC-CATCATGG 3' (SEQ ID NO: 23) and 5' CGAGTCAGCCC-GGGTAATCCGCGGCTAGTTTTTGGTTTCCGCACTG TCCA 3' (SEQ ID NO: 24). Error rate was determined by subcloning 1 µL of the purified PCR product into the pCR™4-TOPO® plasmid and transforming the ligation product into One Shot TOP10 Chemically Competent cells, plating on LB+50 µg/mL Ampicillin plates and growing overnight at 37° C., followed by picking 10 single colonies, growing overnight at 37° C. in LB+50 µg/mL Ampicillin, and then extracting and sequencing the plasmid DNA with the m13-FORWARD (−20) and m13-REVERSE primers. Error rate was determined to be 0.55% by sequencing the DNA fragment from 10 bacterial colonies picked at random. The purified PCR produced was then digested overnight with KpnI-HF and XmaI, repurified, and ligated into an equimolar amount of similarly digested and purified chloramphenicol resistant E. coli expression vector (SEQ ID NO: 9), resulting in 750,000 transformants.

After construction of the library, it was subjected to multiple rounds of genetic selection in the E. coli −ΔtrpE selection cell line in M9-KYN media with decreasing inoculum amounts as described in Example 24 of PCT/US2014/053437, using M9-KYN media that contained M9 minimal salts, 2 mM magnesium sulfate, 0.1 mM calcium chloride, 2% glucose, 10 µM IPTG, 35 µg/mL chloramphenicol, 100 µM Kynurenine, and water, and inoculating with $2*10^7$ cells for Round 1, $2*10^7$ cells for Round 2, $1*10^7$ cells for Round 3, $2*10^6$ cells for Round 4, $1*10^6$ cells for Round 5, $3.3*10^5$ cells for Round 6, $1*10^5$ cells for Round 7, $1*10^5$ cells for Round 8. After plating the final round of E. coli −ΔtrpE selection cells on an LB+35 µg/mL chloramphenicol plate, individual colonies were selected and evaluated for catalytic activity using a microtiter plate kynureninase assay as described in PCT/US2014/053437. Clones displaying greater activity than cells expressing the wild type h-KYNase were sequenced to determine mutations, and subsequently purified to near homogeneity as described in Example 1 and assessed in detail for their steady-state kinetic parameters at 37° C. as described in Example 2. The results of these efforts led to the isolation of two new variants with enhanced kynurenine degrading activity (amino acid SEQ ID NOS: 2 and 3, nucleotide SEQ ID NOS: 27 and 28).

To engineer improved L-Kynurenine degrading activity into an h-KYNase variant with the mutations A99I/G112A/F306Y/I331N/I405L/S408N/A436T (SEQ ID NO: 2), random mutations were introduced in SEQ ID NO: 2 by error-prone PCR of the entire gene. An error-prone PCR library using SEQ ID NO: 27 as template DNA was constructed as described above in Example 5, resulting 165,000,000 transformants with an error rate of 0.45%. After construction of the library, it was subjected to 14 rounds of genetic selection in the E. coli −ΔtrpE selection cell line as described above in Example 5, using the following inoculumn cell counts for Rounds 1-14: $1*10^9$, $5.3*10^8$, $2.7*10^8$, $9*10^7$, $3*10^7$, $1*10^7$, $5*10^6$, $2.5*10^6$, $1*10^6$, $1*10^6$, $1*10^6$, $1*10^6$, $1*10^6$, and $1*10^6$ cells respectively. After plating the final round of E. coli −ΔtrpE selection cells on an LB+35 µg/mL chloramphenicol plate, individual colonies were selected and evaluated for catalytic activity using a microtiter plate kynureninase assay as described in PCT/US2014/053437. Clones displaying greater activity than cells expressing the wild type h-KYNase (SEQ ID NO: 1) were sequenced to determine mutations, and subsequently purified to near homogeneity as described in Example 1 and assessed in detail for their steady-state kinetic parameters at 37° C. as described in Example 2. The results of these efforts led to the isolation of one new variant with enhanced kynurenine degrading activity (amino acid SEQ ID NO: 4; nucleotide SEQ ID NO: 29).

Example 6—Isolation of h-KYNase Variants with Highly Enhanced Kynureninase Activity from Oligonucleotide-Directed Partial Mutagenesis Libraries Focused Around the Active Site Residues Coordinating Substrate Binding A structural and phylogenetic analysis of residues from KYN preferring and OH-KYN preferring enzyme active sites revealed several differences in the identities of $1^{st}$ and $2^{nd}$ shell residues that coordinate substrate binding as defined by those residues within 6 Å of the pyridoxal phosphate cofactor or substrate binding pocket. Differential residues meeting these criteria include for h-KYNU: L72, A99, H102, I110, A136, L137, T138, S221, F225, S332, N333, and Q402. In contrast the most prevalent residues observed in these respective positions for KYN preferring enzymes include (corresponding to h-KYNase numbering): D72, I99, W102, F110, S136, T137, T/S138, P221, Y225, G332, T333, and H402. These distinct active-site amino acid differences suggest that they play a role in substrate discrimination between KYN and OH-KYN. These residues were sometimes near previously determined catalytically important mutations, including N67D, F70L, L72N, and F306/L/W (PCT/US2014/053437). Additional possible mutations of nearby residues of interest included E103Q and H224N to reduce impact of charge imbalances from potential mutations. Thus a degenerate codon library ecompassing N67, F70, L72, A99, H102, E103, P108, I110, A136, L137, T138, S221, H224, F225, F306, I331, S332 and N333, P334, and Q402 was constructed by oligonucleotide-directed mutagenesis of codons corresponding to the above amino acids such that the resulting library of genes could contain either the WT h-KYNU codon or a codon for the mutation of interest, i.e., the amino acid most commonly found in KYN preferring enzymes. After construction and sequence confirmation of a library with 21,000,000 members through ligation into the chloramphenicol resistant E. coli expression vector (SEQ ID NO: 9), as described in Example 5, the library was subjected to 8 rounds of genetic selection in the E. coli −ΔtrpE selection cell line in M9-KYN media with decreasing inoculum amounts as described in Example 5 using the following inoculumn cell counts for Rounds 1-8: $4*10^8$, $2*10^8$, $4*10^7$, $2*10^7$, $1*10^7$, $3*10^6$, $1*10^6$, and $5*10^5$ cells respectively. After plating the final round of E. coli −ΔtrpE selection cells on an LB+35 µg/mL chloramphenicol plate, individual colonies were selected and evaluated for catalytic activity as in Example 5. Clones displaying greater apparent activity than controls were sequenced to determine mutations, and subsequently purified to near homogeneity as described in Example 1 and assessed in detail for their steady-state kinetic parameters at 37° C. as described in Example 2. The results of these efforts led to the isolation of three new variants with enhanced kynurenine degrading activity (amino acid SEQ ID NOS: 5, 6, and 7; nucleotide SEQ ID NOS: 30, 31, and 32).

Example 7—Isolation of an h-KYNase Variant with Highly Enhanced Kynureninase Activity from an Oligonucleotide-Directed Saturated Mutagenesis Library Targeting the Residues Coordinating the Pyridoxal Phosphate Cofactor The phosphate of the essential cofactor PLP has been demonstrated to act as an acid/base catalyst in the mechanism of KYN hydrolysis (Philips et al., *FEBS J.* 2014 February;281(4):1100-9). A structural and phylogenetic analysis of residues from KYN preferring and OH-KYN preferring enzymes revealed differential coordination of the phosphate of PLP. Specifically h-KYNU residues A136/L137 are near the PLP phosphate while KYN preferring enzymes (such as Pf-KYNU (see SEQ ID NO: 1 of PCT/US2015/047475, incorporated herein as SEQ ID NO: 25) have Ser/Thr residues at these residues which donate additional hydrogen bonds to the cofactor. These differences in the active sites suggested that the additional hydrogen bonds to the PLP phosphate in KYN preferring enzymes may mechanistically facilitate the contribution of PLP phosphate to the reaction. Thus an h-KYNU variant with the mutations A99S/F306L/A436T (see SEQ ID NO: 64 of PCT/US2015/047475, incorporated herein as SEQ ID NO: 26), was used as a scaffold to construct an oligonucleotide-directed saturated mutagenesis library of codons corresponding to amino acids 136 and 137. After construction and sequence confirmation of a library with 8,000,000 members through ligation into the chloramphenicol resistant *E. coli* expression vector (SEQ ID NO: 9) as described in Examples 5 and 6, the library was subjected to 5 rounds of genetic selection in the *E. coli* −ΔtrpE selection cell line in M9-KYN media with decreasing inoculum amounts as described in Examples 5 and 6 using the following inoculumn cell counts for Rounds 1-5: $7*10^7$, $1*10^7$, $1*10^6$, $2*10^5$, and $1*10^5$ cells, respectively. After plating the final round of *E. coli* −ΔtrpE selection cells on an LB+35 µg/mL chloramphenicol plate, individual colonies were selected and evaluated for catalytic activity as in Examples 5 and 6. Clones displaying greater apparent activity than controls were sequenced to determine mutations, and subsequently purified to near homogeneity as described in Example 1 and assessed in detail for their steady-state kinetic parameters at 37° C. as described in Example 2. The results of these efforts led to the isolation of one new variant with enhanced kynurenine degrading activity (amino acid SEQ ID NO: 8; nucleotide SEQ ID NO: 33).

Example 8—Comparison of the Kynurieninase Activity of the h-KYNU Variants Described Above to Wild Type h-KYNU The following table is a compilation of data comparing the kynurieninase activity of the h-KYNU variants described above to wild type h-KYNU, the results of which demonstrate that the surprising improvements in activity achieved as compared to the human enzyme. These assays were carried out as described above, and are compiled in the following table, Table 1:

TABLE 1 h-KYNU Variants with Improved Activity

| SEQ ID NO. | Variant | $k_{cat}/K_M$ ($s^{-1}mM^{-1}$) | Fold change from WT |
|---|---|---|---|
| 2 | A99I/G112A/F306Y/I331N/I405L/S408N/A436T | 5.5 | 55 |
| 3 | A99I/G112A/K191E/F306Y/A381S/I405L/S408N/A436T | 5.9 | 59 |
| 4 | Q14R/A99I/G112A/M189I/H230Y/F306Y/I331N/I405L/S408N/A436T | 7.0 | 70 |
| 5 | T138S/H224N/F225Y/F306W/N333T/S408N/A436T | 0.6 | 6 |
| 6 | N67D/L72N/E103Q/F225Y/I331V/S408N/A436T | 3.2 | 32 |
| 7 | N67D/A136S/T138S/F225Y/S408N/A436T | 1.2 | 12 |
| 8 | A99S/A136G/L137T/F306L/A436T | 2.6 | 26 |

Example 9—Systemic Kynurenine Depletion by PEG-Hs-KYNU (SEQ ID NO:2) Therapy in the Syngeneic CT26 Mouse Colon Carcinoma Model The ability of the PEGylated human kynureninase variant (PEG-hs-KYNU, SEQ ID NO:2) to deplete serum kynurenine levels was evaluated in the IDO1-expressing CT26 colon carcinoma mouse model. Tumors were initiated by implanting 50,000 CT26 cells in the flanks of Balb/c mice (Day 0, n=12 mice total, n=4 mice for each time point). Once the tumors reached a mean volume of 60 mm³ (Day 14), the animals were treated with 1.25 mg of PEG-hs-KYNU (SEQ ID NO:2) by peri-tumoral injection. Plasma kynurenine levels were assessed by mass spectrometry after 6 hours, and 24 hours (n=4 mice per time point) (FIG. 1). Baseline Kyn levels were determined by administering 1.25 mg of heat inactivated PEG-hs-KYNU by peri-tumoral injection and assessed by mass spectometry 24 hrs post dosing (n=4 mice). Administration of PEG-hs-KYNU (SEQ ID NO:2) resulted in systemic kynurenine depletion 6 hours and 24 hours after treatment.

Figure 2:
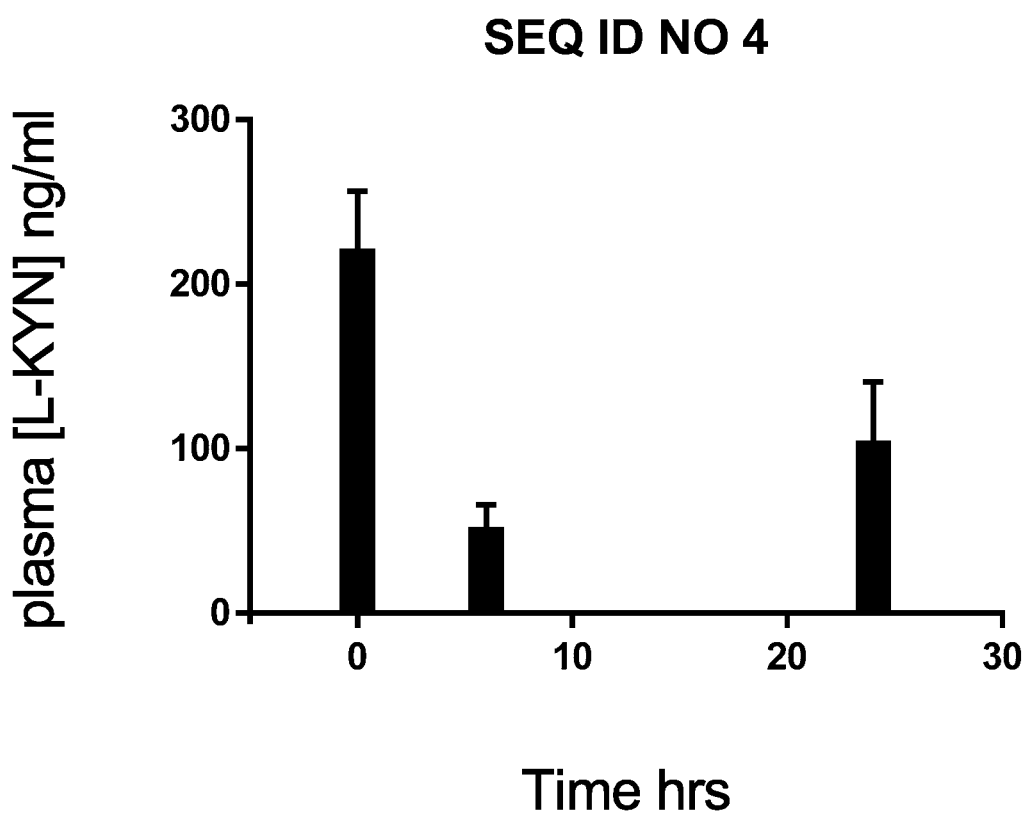
FIG. 2: Mice bearing CT26 tumors (n=4 each time point) were injected with 50 mg/kg PEGylated kynureninase (SEQ ID NO:4) by peri-tumoral injection at time=0 hours, and plasma KYN levels were assessed by mass spectrometry at 0, 6, and 24 hours.

Example 10—Systemic Kynurenine Depletion by PEG-Hs-KYNU (SEQ ID NO:4) Therapy in the Syngeneic CT26 Mouse Colon Carcinoma Model The ability of the PEGylated human kynureninase variant (PEG-hs-KYNU, SEQ ID NO:4) to depleted serum kynurenine levels was also evaluated in the CT26 colon carcinoma mouse model. Tumors were initiated by implanting 50,000 CT26 cells in the flanks of Balb/c mice (Day 0, n=12 mice total, n=4 mice for each time point). Once the tumors reached a mean volume of 60 mm³ (Day 14), the animals were treated with 1.25 mg of PEG-hs-KYNU (SEQ ID NO 4) by peri-tumoral injection. Plasma kynurenine levels were assessed by mass spectrometry after 6 hours, and 24 hours (n=4 mice per time point) (FIG. 2). Baseline Kyn levels were determined by administering 1.25 mg of heat inactivated PEG-hs-KYNU by peri-tumoral injection and assessed by mass spec 24 hrs post dosing (n=4 mice). Administration of PEG-hs-KYNU (SEQ ID NO:4) resulted in systemic kynurenine depletion 6 hours and 24 hours after treatment.

Example 11—Determination of Plasma KYN Levels by LC-MS

Following collection from mice of Examples 9 and 10, blood samples were kept on ice at all times until addition to pre-chilled EDTA-K2 anticoagulant tubes. Plasma was then collected by centrifugation at 4° C. for 5 min to remove cellular debris. A 50 µL aliquot of plasma was then added into pre-chilled tubes containing 200 µL internal standard (200 ng/mL 13C4, 15N-Kynurenine in ACN/MeOH(v:v, 25:75) with 0.3% formic acdi and 0.1 mol/L citric acid) and centrifuged at 13000 rpm in a microcentrifuge for 10 min, 4° C. Kyn levels were then assessed by UPLC-MS using a 4000 Q TRAP system by applying samples to an ACE 3 AQ 2.1*100 mm, 3 µm column (Phenomenex) under a Mobile Phase consisting of 99% 0.1% formic acid in water (mobile phase A) and 1% 0.5% formic acid in acetonitrile (mobile phase B) at a flow rate of 0.7 ml/min. Kyn and internal standard is subsequently eluted by a stepwise gradient of 95% Mobile phase B and detected by ESI in positive mode. Plasma Kyn levels were then quantitated ratiometrically using the 13C4, 15N-Kynurenine internal standard.

Figure 3:
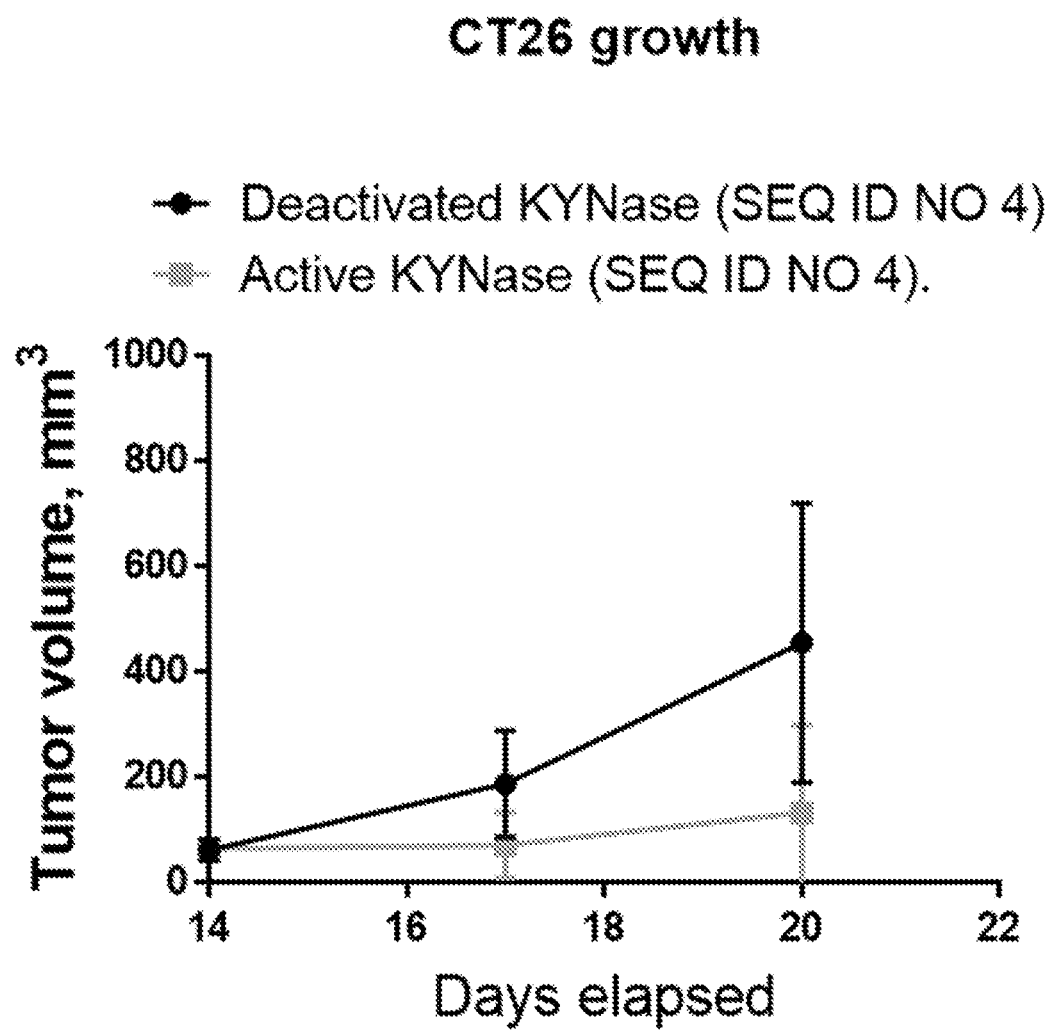
FIG. 3: Mice (n=9 mice treated group, n=8 mice control group) were inoculated with $5 \times 10^4$ CT26 cells and allowed to develop tumors until day 14 at which point they were treated with 20 mg/kg PEGylated kynureninase (SEQ ID NO:4) by peri-tumoral injection every three days. As a control, one group was treated with the same dosing schedule using heat deactivated PEGylated kynureninase (SEQ ID NO:4).

Example 12—Efficacy of PEG-Hs-KYNU Therapies in the Syngeneic CT26 Mouse Colon Carcinoma Model The PEGylated human kynureninase variant (PEG-hs-KYNU, SEQ ID NO:4) was evaluated in the CT26 colon carcinoma mouse model. Tumors were initiated by implanting 50,000 CT26 cells in the flanks of Balb/c mice (Day 0, n=9 mice treated group, n=8 mice control group). Once the tumors reached a mean volume of 60 mm$^3$ (Day 14), the animals were treated with 500 µg of PEG-hs-KYNU (SEQ ID NO:4) by subcutaneous injection near the tumor site every three days for a total of 6 doses. An identical treatment regimen with heat-inactivated PEG-hs-KYNU (SEQ ID NO:4) was used as a control. Administration of PEG-hs-KYNU (SEQ ID NO:4) resulted in drastic tumor growth retardation (FIG. 3) with 33% of the treated mice displaying complete tumor regression.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

Ahmed et al., HER2-specific T cells target primary glioblastoma stem cells and induce regression of autologous experimental tumors. *Clinical Cancer Research*, 16(2): 474-485, 2010.
Austin-Ward and Villaseca, *Revista Medica de Chile*, 126 (7):838-845, 1998.
Ausubel et al., Current Protocols in Molecular Biology, Greene Publishing Associates and Wiley Interscience, N.Y., 1994.
Bukowski et al., *Clinical Cancer Res.*, 4(10):2337-2347, 1998.
Chen and Guillemin, Kynurenine pathway metabolites in humans: disease and healthy States. *Int J Tryptophan Res*, 2:1-19, 2009.
Christodoulides et al., *Microbiology*, 144(Pt 11):3027-3037, 1998.
Cole and Gaucher, Exploiting models of molecular evoluation to efficiently direct protein engineering. *J. Mol. Evol.*, 72:193, 2011.
Curran et al., PD-1 and CTLA-4 combination blockade expands infiltrating T cells and reduces regulatory T and myeloid cells within B16 melanoma tumors. *Proceedings of the National Academy of Sciences*, 107:4275-4280, 2010.
Davidson et al., *J. Immunother* 21(5):389-398, 1998.
de Jong et al., Serum tryptophan and kynurenine concentrations as parameters for indoleamine 2,3-dioxygenase activity in patients with endometrial, ovarian, and vulvar cancer. *Int J Gynecol Cancer*, 21(7):1320-1327, 2011.
Della Chiesa et al., The tryptophan catabolite L-kynurenine inhibits the surface expression of NKp46-and NKG2D-activating receptors and regulates NK-cell function. *Blood*, 108(13):4118-4125, 2006.
Godin-Ethier et al., Indoleamine 2, 3-Dioxygenase Expression in Human Cancers: Clinical and Immunologic Perspectives. *Clinical Cancer Research*, 17(22):6985-6991, 2011.
Hanibuchi et al., *Int. J. Cancer*, 78(4):480-485, 1998.
Harkki et al., *BioTechnology*, 7:596-603, 1989.
Hellstrand et al., *Acta Oncologica*, 37(4):347-353, 1998.
Hollander, *Front. Immun.*, 3:3, 2012.
Holmgaard et al., Indoleamine 2, 3-dioxygenase is a critical resistance mechanism in antitumor T cell immunotherapy targeting CTLA-4. *The Journal of Experimental Medicine*, 210:1389-1402, 2013.
Hoover and Lubkowski, DNAWorks: an automated method for designing oligonucleotides for PCR-based gene synthesis. *Nucleic Acids Research*, 30(10):e43-e43, 2002.
Hopwood et al., In: *Genetic Manipulation of Streptomyces*, A Laboratory Manual, The John Innes Foundation, Norwich, Conn., 1985.
Hui and Hashimoto, *Infection Immun.*, 66(11):5329-5336, 1998.
Ito et al., *J. Biochem.*, 79:1263, 1976.
Kaper et al., Nanosensor detection of an immunoregulatory tryptophan influx/kynurenine efflux cycle. *PLoS Biology*, 5(10):e257, 2007.
Lipowska-Bhalla et al., Targeted immunotherapy of cancer with CAR T cells: achievements and challenges. *Cancer Immunology Immunotherapy*, 61(7):953-962, 2012.
Lob et al., Inhibitors of indoleamine-2,3-dioxygenase for cancer therapy: can we see the wood for the trees? *Nat Rev Cancer*, 9(6):445-452, 2009.
Lordanescu, *J Bacteriol*, 12:597 601, 1975.
Mandi and Vecsei, The kynurenine system and immunoregulation. *J Neural Transm*, 119(2):197-209, 2012.
Maniatis, et al., Molecular Cloning, A Laboratory Manual, Cold Spring Harbor Press, Cold Spring Harbor, N.Y., 1988.
Mellor et al., *Gene*, 24:1-14, 1983.
Mezrich et al., An interaction between kynurenine and the aryl hydrocarbon receptor can generate regulatory T cells. *The Journal of Immunology*, 185 (6): 3190-3198, 2010.
Opitz et al., The Indoleamine-2, 3-Dioxygenase (IDO) Inhibitor 1-Methyl-D-tryptophan Upregulates IDO1 in Human Cancer Cells. *PLoS One*, 6(5):e19823, 2011.

Opitz et al., An endogenous tumour-promoting ligand of the human aryl hydrocarbon receptor. *Nature*, 478(7368): 197-203, 2011.

Penttila et al., *Gene*, 61:155-164, 1987.

Pilotte et al., Reversal of tumoral immune resistance by inhibition of tryptophan 2,3-dioxygenase. *Proc Natl Acad Sci USA*, 109(7):2497-2502, 2012.

Prendergast, Cancer: Why tumours eat tryptophan. *Nature*, 478(7368):192-194, 2011.

Qin et al., *Proc. Natl. Acad. Sci. USA*, 95(24):14411-14416, 1998.

Remington's Pharmaceutical Sciences, 18th Ed. Mack Printing Company, 1289-1329, 1990.

Rutella et al., Targeting indoleamine 2,3-dioxygenase (IDO) to counteract tumour-induced immune dysfunction: from biochemistry to clinical development. *Endocr Metab Immune Disord Drug Targets*, 9(2):151-177, 2009.

Schellenberger et al., *Nature Biotech.*, 27:1186-1190, 2009.

Shin et al., Modulation of natural killer cell antitumor activity by the aryl hydrocarbon receptor. *Proc Natl Acad Sci USA*, 110(30):12391-12396, 2013.

Sibakov et al., *Eur. J. Biochem.*, 145:567 572, 1984.

Song et al., L-Kynurenine-induced apoptosis in human NK cells is mediated by reactive oxygen species. *International Immunopharmacology*, 11(8):932-938, 2011.

Stone et al., Replacing $Mn^{2+}$ with $Co^{2+}$ in human arginase I enhances cytotoxicity toward L-arginine auxotrophic cancer cell lines. *ACS Chemical Biology*, 5:333-342, 2010.

Voigt et al., Protein building blocks preserved by recombination. *Nature Structural & Molecular Biology*, 9:553, 2002.

Ward, Proc, Embo-Alko Workshop on Molecular Biology of Filamentous Fungi, Helsinki, 119-128, 1989.

Wawrzynczak and Thorpe, In: *Immunoconjugates, Antibody Conuugates In Radioimaging And Therapy Of Cancer*, Vogel (Ed.), NY, Oxford University Press, 28, 1987.

Yao et al., Serum metabolic profiling and features of papillary thyroid carcinoma and nodular goiter. *Mol Biosyst*, 7(9):2608-2614, 2011.

Yoshikawa et al., Serum concentration of L-kynurenine predicts the clinical outcome of patients with diffuse large B-cell lymphoma treated with R-CHOP. *Eur J Haematol*, 84(4):304-309, 2010.

What is claimed is:

1. An isolated, modified human kynureninase enzyme, said modified enzyme comprising a mutation set relative to native human kynureninase (see SEQ ID NO: 1), wherein the mutation set is selected from the group consisting of the following mutation sets: (a) A99I, G112A, F306Y, I331N, I405L, S408N and A436T; (b) A99I, G112A, K191E, F306Y, A381S, I405L, S408N and A436T; (c) Q14R, A99I, G112A, M189I, H230Y, F306Y, I331N, I405L, S408N and A436T; (d) T138S, H224N, F225Y, F306W, N333T, S408N and A436T; (e) N67D, L72N, E103Q, F225Y, I331V, S408N and A436T; (f) N67D, A136S, T138S, F225Y, S408N and A436T; and (g) A99S, A136G, L137T, F306L and A436T.

2. The enzyme of claim 1, further comprising a heterologous peptide segment.

3. The enzyme of claim 1, wherein the enzyme is coupled to polyethylene glycol (PEG).

4. The enzyme of claim 3, wherein the enzyme is coupled to PEG via one or more Lys or Cys residues.

5. A nucleic acid comprising a nucleotide sequence encoding the enzyme of claim 1.

6. The nucleic acid of claim 5, wherein the nucleic acid is codon optimized for expression in bacteria, fungus, insects, or mammals.

7. An expression vector comprising the nucleic acid of claim 5.

8. A host cell comprising the nucleic acid of claim 7.

9. The host cell of claim 8, wherein the host cell is a bacterial cell, a fungal cell, an insect cell, or a mammalian cell.

10. A pharmaceutical formulation comprising the enzyme of claim 1 in a pharmaceutically acceptable carrier.

11. A transgenic T cell comprising an expressed chimeric antigen T-cell receptor (CAR) and an expressed kynureninase enzyme according to claim 1.

12. The cell of claim 11, wherein the cell is a human T cell.

13. The cell of claim 11, wherein the CAR is targeted to a cancer-cell antigen.

* * * * *

```
                         SEQUENCE LISTING

<160> NUMBER OF SEQ ID NOS: 34

<210> SEQ ID NO 1
<211> LENGTH: 465
<212> TYPE: PRT
<213> ORGANISM: Homo sapiens

<400> SEQUENCE: 1

Met Glu Pro Ser Ser Leu Glu Leu Pro Ala Asp Thr Val Gln Arg Ile
1               5                   10                  15

Ala Ala Glu Leu Lys Cys His Pro Thr Asp Glu Arg Val Ala Leu His
                20                  25                  30

Leu Asp Glu Glu Asp Lys Leu Arg His Phe Arg Glu Cys Phe Tyr Ile
            35                  40                  45

Pro Lys Ile Gln Asp Leu Pro Pro Val Asp Leu Ser Leu Val Asn Lys
        50                  55                  60

Asp Glu Asn Ala Ile Tyr Phe Leu Gly Asn Ser Leu Gly Leu Gln Pro
65                  70                  75                  80

Lys Met Val Lys Thr Tyr Leu Glu Glu Glu Leu Asp Lys Trp Ala Lys
                85                  90                  95

Ile Ala Ala Tyr Gly His Glu Val Gly Lys Arg Pro Trp Ile Thr Gly
                100                 105                 110

Asp Glu Ser Ile Val Gly Leu Met Lys Asp Ile Val Gly Ala Asn Glu
            115                 120                 125

Lys Glu Ile Ala Leu Met Asn Ala Leu Thr Val Asn Leu His Leu Leu
        130                 135                 140

Met Leu Ser Phe Phe Lys Pro Thr Pro Lys Arg Tyr Lys Ile Leu Leu
145                 150                 155                 160

Glu Ala Lys Ala Phe Pro Ser Asp His Tyr Ala Ile Glu Ser Gln Leu
                165                 170                 175

Gln Leu His Gly Leu Asn Ile Glu Glu Ser Met Arg Met Ile Lys Pro
            180                 185                 190

Arg Glu Gly Glu Glu Thr Leu Arg Ile Glu Asp Ile Leu Glu Val Ile
        195                 200                 205

Glu Lys Glu Gly Asp Ser Ile Ala Val Ile Leu Phe Ser Gly Val His
        210                 215                 220
```

```
Phe Tyr Thr Gly Gln His Phe Asn Ile Pro Ala Ile Thr Lys Ala Gly
225                 230                 235                 240

Gln Ala Lys Gly Cys Tyr Val Gly Phe Asp Leu Ala His Ala Val Gly
            245                 250                 255

Asn Val Glu Leu Tyr Leu His Asp Trp Gly Val Asp Phe Ala Cys Trp
        260                 265                 270

Cys Ser Tyr Lys Tyr Leu Asn Ala Gly Ala Gly Ile Ala Gly Ala
    275                 280                 285

Phe Ile His Glu Lys His Ala His Thr Ile Lys Pro Ala Leu Val Gly
290                 295                 300

Trp Phe Gly His Glu Leu Ser Thr Arg Phe Lys Met Asp Asn Lys Leu
305                 310                 315                 320

Gln Leu Ile Pro Gly Val Cys Gly Phe Arg Ile Ser Asn Pro Pro Ile
                325                 330                 335

Leu Leu Val Cys Ser Leu His Ala Ser Leu Glu Ile Phe Lys Gln Ala
            340                 345                 350

Thr Met Lys Ala Leu Arg Lys Lys Ser Val Leu Leu Thr Gly Tyr Leu
        355                 360                 365

Glu Tyr Leu Ile Lys His Asn Tyr Gly Lys Asp Lys Ala Ala Thr Lys
    370                 375                 380

Lys Pro Val Val Asn Ile Ile Thr Pro Ser His Val Glu Glu Arg Gly
385                 390                 395                 400

Cys Gln Leu Thr Ile Thr Phe Ser Val Pro Asn Lys Asp Val Phe Gln
                405                 410                 415

Glu Leu Glu Lys Arg Gly Val Val Cys Asp Lys Arg Asn Pro Asn Gly
            420                 425                 430

Ile Arg Val Ala Pro Val Pro Leu Tyr Asn Ser Phe His Asp Val Tyr
        435                 440                 445

Lys Phe Thr Asn Leu Leu Thr Ser Ile Leu Asp Ser Ala Glu Thr Lys
    450                 455                 460

Asn
465

<210> SEQ ID NO 2
<211> LENGTH: 465
<212> TYPE: PRT
<213> ORGANISM: Artificial sequence
<220> FEATURE:
<223> OTHER INFORMATION: Synthetic polypeptide

<400> SEQUENCE: 2

Met Glu Pro Ser Ser Leu Glu Leu Pro Ala Asp Thr Val Gln Arg Ile
1               5                   10                  15

Ala Ala Glu Leu Lys Cys His Pro Thr Asp Gly Arg Val Ala Leu His
            20                  25                  30

Leu Asp Glu Glu Asp Lys Leu Arg His Phe Arg Glu Cys Phe Tyr Ile
        35                  40                  45

Pro Lys Ile Gln Asp Leu Pro Pro Val Asp Leu Ser Leu Val Asn Lys
    50                  55                  60

Asp Glu Asn Ala Ile Tyr Phe Leu Gly Asn Ser Leu Gly Leu Gln Pro
65                  70                  75                  80

Lys Met Val Lys Thr Tyr Leu Glu Glu Glu Leu Asp Lys Trp Ala Lys
                85                  90                  95

Ile Ala Ile Tyr Gly His Glu Val Gly Lys Arg Pro Trp Ile Thr Ala
            100                 105                 110
```

Asp Glu Ser Ile Val Gly Leu Met Lys Asp Ile Val Gly Ala Asn Glu
            115                 120                 125

Lys Glu Ile Ala Leu Met Asn Ala Leu Thr Val Asn Leu His Leu Leu
        130                 135                 140

Met Leu Ser Phe Phe Lys Pro Thr Pro Lys Arg Tyr Lys Ile Leu Leu
145                 150                 155                 160

Glu Ala Lys Ala Phe Pro Ser Asp His Tyr Ala Ile Glu Ser Gln Leu
                165                 170                 175

Gln Leu His Gly Leu Asn Ile Glu Glu Ser Met Arg Met Ile Lys Pro
            180                 185                 190

Arg Glu Gly Glu Thr Leu Arg Ile Glu Asp Ile Leu Glu Val Ile
        195                 200                 205

Glu Lys Glu Gly Asp Ser Ile Ala Val Ile Leu Phe Ser Gly Val His
        210                 215                 220

Phe Tyr Thr Gly Gln His Phe Asn Ile Pro Ala Ile Thr Lys Ala Gly
225                 230                 235                 240

Gln Ala Lys Gly Cys Tyr Val Gly Phe Asp Leu Ala His Ala Val Gly
                245                 250                 255

Asn Val Glu Leu Tyr Leu His Asp Trp Gly Val Asp Phe Ala Cys Trp
            260                 265                 270

Cys Ser Tyr Lys Tyr Leu Asn Ala Gly Ala Gly Ile Ala Gly Ala
        275                 280                 285

Phe Ile His Glu Lys His Ala His Thr Ile Lys Pro Ala Leu Val Gly
290                 295                 300

Trp Tyr Gly His Glu Leu Ser Thr Arg Phe Lys Met Asp Asn Lys Leu
305                 310                 315                 320

Gln Leu Ile Pro Gly Val Cys Gly Phe Arg Asn Ser Asn Pro Pro Ile
                325                 330                 335

Leu Leu Val Cys Ser Leu His Ala Ser Leu Glu Ile Phe Lys Gln Ala
            340                 345                 350

Thr Met Lys Ala Leu Arg Lys Lys Ser Val Leu Leu Thr Gly Tyr Leu
        355                 360                 365

Glu Tyr Leu Ile Lys His Asn Tyr Gly Lys Asp Lys Ala Ala Thr Lys
        370                 375                 380

Lys Pro Val Val Asn Ile Ile Thr Pro Ser His Val Glu Glu Arg Gly
385                 390                 395                 400

Cys Gln Leu Thr Leu Thr Phe Asn Val Pro Asn Lys Asp Val Phe Gln
                405                 410                 415

Glu Leu Glu Lys Arg Gly Val Val Cys Asp Lys Arg Asn Pro Asn Gly
            420                 425                 430

Ile Arg Val Thr Pro Val Pro Leu Tyr Asn Ser Phe His Asp Val Tyr
        435                 440                 445

Lys Phe Thr Asn Leu Leu Thr Ser Ile Leu Asp Ser Ala Glu Thr Lys
    450                 455                 460

Asn
465

<210> SEQ ID NO 3
<211> LENGTH: 465
<212> TYPE: PRT
<213> ORGANISM: Artificial sequence
<220> FEATURE:
<223> OTHER INFORMATION: Synthetic polypeptide

<400> SEQUENCE: 3

```
Met Glu Pro Ser Ser Leu Glu Leu Pro Ala Asp Thr Val Gln Arg Ile
1               5                   10                  15

Ala Ala Glu Leu Lys Cys His Pro Thr Asp Glu Arg Val Ala Leu His
            20                  25                  30

Leu Asp Glu Glu Asp Lys Leu Arg His Phe Arg Glu Cys Phe Tyr Ile
        35                  40                  45

Pro Lys Ile Gln Asp Leu Pro Pro Val Asp Leu Ser Leu Val Asn Lys
    50                  55                  60

Asp Glu Asn Ala Ile Tyr Phe Leu Gly Asn Ser Leu Gly Leu Gln Pro
65              70                  75                  80

Lys Met Val Lys Thr Tyr Leu Glu Glu Leu Asp Lys Trp Ala Lys
                85                  90                  95

Ile Ala Ile Tyr Gly His Glu Val Gly Lys Arg Pro Trp Ile Thr Ala
                100                 105                 110

Asp Glu Ser Ile Val Gly Leu Met Lys Asp Ile Val Gly Ala Asn Glu
            115                 120                 125

Lys Glu Ile Ala Leu Met Asn Ala Leu Thr Val Asn Leu His Leu Leu
    130                 135                 140

Met Leu Ser Phe Phe Lys Pro Thr Pro Lys Arg Tyr Lys Ile Leu Leu
145                 150                 155                 160

Glu Ala Lys Ala Phe Pro Ser Asp His Tyr Ala Ile Glu Ser Gln Leu
                165                 170                 175

Gln Leu His Gly Leu Asn Ile Glu Glu Ser Met Arg Met Ile Glu Pro
            180                 185                 190

Arg Glu Gly Glu Glu Thr Leu Arg Ile Glu Asp Ile Leu Glu Val Ile
        195                 200                 205

Glu Lys Glu Gly Asp Ser Ile Ala Val Ile Leu Phe Ser Gly Val His
    210                 215                 220

Phe Tyr Thr Gly Gln His Phe Asn Ile Pro Ala Ile Thr Lys Ala Gly
225                 230                 235                 240

Gln Ala Lys Gly Cys Tyr Val Gly Phe Asp Leu Ala His Ala Val Gly
                245                 250                 255

Asn Val Glu Leu Tyr Leu His Asp Trp Gly Val Asp Phe Ala Cys Trp
            260                 265                 270

Cys Ser Tyr Lys Tyr Leu Asn Ala Gly Ala Gly Gly Ile Ala Gly Ala
        275                 280                 285

Phe Ile His Glu Lys His Ala His Thr Ile Lys Pro Ala Leu Val Gly
    290                 295                 300

Trp Tyr Gly His Glu Leu Ser Thr Arg Phe Lys Met Asp Asn Lys Leu
305                 310                 315                 320

Gln Leu Ile Pro Gly Val Cys Gly Phe Arg Ile Ser Asn Pro Pro Ile
                325                 330                 335

Leu Leu Val Cys Ser Leu His Ala Ser Leu Glu Ile Phe Lys Gln Ala
            340                 345                 350

Thr Met Lys Ala Leu Arg Lys Lys Ser Val Leu Leu Thr Gly Tyr Leu
        355                 360                 365

Glu Tyr Leu Ile Lys His Asn Tyr Gly Lys Asp Lys Ser Ala Thr Lys
    370                 375                 380

Lys Pro Val Val Asn Ile Ile Thr Pro Ser His Val Glu Glu Arg Gly
385                 390                 395                 400

Cys Gln Leu Thr Leu Thr Phe Asn Val Pro Asn Lys Asp Val Phe Gln
                405                 410                 415
```

```
Glu Leu Glu Lys Arg Gly Val Val Cys Asp Lys Arg Asn Pro Asn Gly
            420                 425                 430

Ile Arg Val Thr Pro Val Pro Leu Tyr Asn Ser Phe His Asp Val Tyr
            435                 440                 445

Lys Phe Thr Asn Leu Leu Thr Ser Ile Leu Asp Ser Ala Glu Thr Lys
            450                 455                 460

Asn
465

<210> SEQ ID NO 4
<211> LENGTH: 465
<212> TYPE: PRT
<213> ORGANISM: Artificial sequence
<220> FEATURE:
<223> OTHER INFORMATION: Synthetic polypeptide

<400> SEQUENCE: 4

Met Glu Pro Ser Ser Leu Glu Leu Pro Ala Asp Thr Val Arg Arg Ile
1               5                   10                  15

Ala Ala Glu Leu Lys Cys His Pro Thr Asp Glu Arg Val Ala Leu His
            20                  25                  30

Leu Asp Glu Glu Asp Lys Leu Arg His Phe Arg Glu Cys Phe Tyr Ile
        35                  40                  45

Pro Lys Ile Gln Asp Leu Pro Pro Val Asp Leu Ser Leu Val Asn Lys
    50                  55                  60

Asp Glu Asn Ala Ile Tyr Phe Leu Gly Asn Ser Leu Gly Leu Gln Pro
65                  70                  75                  80

Lys Met Val Lys Thr Tyr Leu Glu Glu Leu Asp Lys Trp Ala Lys
                85                  90                  95

Ile Ala Ile Tyr Gly His Glu Val Gly Lys Arg Pro Trp Ile Thr Ala
            100                 105                 110

Asp Glu Ser Ile Val Gly Leu Met Lys Asp Ile Val Gly Ala Asn Glu
            115                 120                 125

Lys Glu Ile Ala Leu Met Asn Ala Leu Thr Val Asn Leu His Leu Leu
130                 135                 140

Met Leu Ser Phe Phe Lys Pro Thr Pro Lys Arg Tyr Lys Ile Leu Leu
145                 150                 155                 160

Glu Ala Lys Ala Phe Pro Ser Asp His Tyr Ala Ile Glu Ser Gln Leu
            165                 170                 175

Gln Leu His Gly Leu Asn Ile Glu Glu Ser Met Arg Ile Ile Lys Pro
            180                 185                 190

Arg Glu Gly Glu Glu Thr Leu Arg Ile Glu Asp Ile Leu Glu Val Ile
            195                 200                 205

Glu Lys Glu Gly Asp Ser Ile Ala Val Ile Leu Phe Ser Gly Val His
            210                 215                 220

Phe Tyr Thr Gly Gln Tyr Phe Asn Ile Pro Ala Ile Thr Lys Ala Gly
225                 230                 235                 240

Gln Ala Lys Gly Cys Tyr Val Gly Phe Asp Leu Ala His Ala Val Gly
                245                 250                 255

Asn Val Glu Leu Tyr Leu His Asp Trp Gly Val Asp Phe Ala Cys Trp
            260                 265                 270

Cys Ser Tyr Lys Tyr Leu Asn Ala Gly Ala Gly Gly Ile Ala Gly Ala
            275                 280                 285

Phe Ile His Glu Lys His Ala Thr Ile Lys Pro Ala Leu Val Gly
    290                 295                 300
```

```
Trp Tyr Gly His Glu Leu Ser Thr Arg Phe Lys Met Asp Asn Lys Leu
305                 310                 315                 320

Gln Leu Ile Pro Gly Val Cys Gly Phe Arg Asn Ser Asn Pro Pro Ile
                325                 330                 335

Leu Leu Val Cys Ser Leu His Ala Ser Leu Glu Ile Phe Lys Gln Ala
            340                 345                 350

Thr Met Lys Ala Leu Arg Lys Lys Ser Val Leu Leu Thr Gly Tyr Leu
        355                 360                 365

Glu Tyr Leu Ile Lys His Asn Tyr Gly Lys Asp Lys Ala Ala Thr Lys
    370                 375                 380

Lys Pro Val Val Asn Ile Ile Thr Pro Ser His Val Glu Glu Arg Gly
385                 390                 395                 400

Cys Gln Leu Thr Leu Thr Phe Asn Val Pro Asn Lys Asp Val Phe Gln
                405                 410                 415

Glu Leu Glu Lys Arg Gly Val Val Cys Asp Lys Arg Asn Pro Asn Gly
            420                 425                 430

Ile Arg Val Thr Pro Val Pro Leu Tyr Asn Ser Phe His Asp Val Tyr
        435                 440                 445

Lys Phe Thr Asn Leu Leu Thr Ser Ile Leu Asp Ser Ala Glu Thr Lys
    450                 455                 460

Asn
465

<210> SEQ ID NO 5
<211> LENGTH: 465
<212> TYPE: PRT
<213> ORGANISM: Artificial sequence
<220> FEATURE:
<223> OTHER INFORMATION: Synthetic polypeptide

<400> SEQUENCE: 5

Met Glu Pro Ser Ser Leu Glu Leu Pro Ala Asp Thr Val Gln Arg Ile
1               5                   10                  15

Ala Ala Glu Leu Lys Cys His Pro Thr Asp Glu Arg Val Ala Leu His
            20                  25                  30

Leu Asp Glu Glu Asp Lys Leu Arg His Phe Arg Glu Cys Phe Tyr Ile
        35                  40                  45

Pro Lys Ile Gln Asp Leu Pro Pro Val Asp Leu Ser Leu Val Asn Lys
    50                  55                  60

Asp Glu Asn Ala Ile Tyr Phe Leu Gly Asn Ser Leu Gly Leu Gln Pro
65                  70                  75                  80

Lys Met Val Lys Thr Tyr Leu Glu Glu Glu Leu Asp Lys Trp Ala Lys
                85                  90                  95

Ile Ala Ala Tyr Gly His Glu Val Gly Lys Arg Pro Trp Ile Thr Gly
            100                 105                 110

Asp Glu Ser Ile Val Gly Leu Met Lys Asp Ile Val Gly Ala Asn Glu
        115                 120                 125

Lys Glu Ile Ala Leu Met Asn Ala Leu Ser Val Asn Leu His Leu Leu
    130                 135                 140

Met Leu Ser Phe Phe Lys Pro Thr Pro Lys Arg Tyr Lys Ile Leu Leu
145                 150                 155                 160

Glu Ala Lys Ala Phe Pro Ser Asp His Tyr Ala Ile Glu Ser Gln Leu
                165                 170                 175

Gln Leu His Gly Leu Asn Ile Glu Glu Ser Met Arg Met Ile Lys Pro
            180                 185                 190
```

Arg Glu Gly Glu Glu Thr Leu Arg Ile Glu Asp Ile Leu Glu Val Ile
            195                 200                 205

Glu Lys Glu Gly Asp Ser Ile Ala Val Ile Leu Phe Ser Gly Val Asn
    210                 215                 220

Tyr Tyr Thr Gly Gln His Phe Asn Ile Pro Ala Ile Thr Lys Ala Gly
225                 230                 235                 240

Gln Ala Lys Gly Cys Tyr Val Gly Phe Asp Leu Ala His Ala Val Gly
                245                 250                 255

Asn Val Glu Leu Tyr Leu His Asp Trp Gly Val Asp Phe Ala Cys Trp
            260                 265                 270

Cys Ser Tyr Lys Tyr Leu Asn Ala Gly Ala Gly Ile Ala Gly Ala
        275                 280                 285

Phe Ile His Glu Lys His Ala His Thr Ile Lys Pro Ala Leu Val Gly
            290                 295                 300

Trp Trp Gly His Glu Leu Ser Thr Arg Phe Lys Met Asp Asn Lys Leu
305                 310                 315                 320

Gln Leu Ile Pro Gly Val Cys Gly Phe Arg Ile Ser Thr Pro Pro Ile
                325                 330                 335

Leu Leu Val Cys Ser Leu His Ala Ser Leu Glu Ile Phe Lys Gln Ala
            340                 345                 350

Thr Met Lys Ala Leu Arg Lys Lys Ser Val Leu Leu Thr Gly Tyr Leu
        355                 360                 365

Glu Tyr Leu Ile Lys His Asn Tyr Gly Lys Asp Lys Ala Ala Thr Lys
    370                 375                 380

Lys Pro Val Val Asn Ile Ile Thr Pro Ser His Val Glu Glu Arg Gly
385                 390                 395                 400

Cys Gln Leu Thr Ile Thr Phe Asn Val Pro Asn Lys Asp Val Phe Gln
                405                 410                 415

Glu Leu Glu Lys Arg Gly Val Val Cys Asp Lys Arg Asn Pro Asn Gly
            420                 425                 430

Ile Arg Val Thr Pro Val Pro Leu Tyr Asn Ser Phe His Asp Val Tyr
        435                 440                 445

Lys Phe Thr Asn Leu Leu Thr Ser Ile Leu Asp Ser Ala Glu Thr Lys
    450                 455                 460

Asn
465

<210> SEQ ID NO 6
<211> LENGTH: 465
<212> TYPE: PRT
<213> ORGANISM: Artificial sequence
<220> FEATURE:
<223> OTHER INFORMATION: Synthetic polypeptide

<400> SEQUENCE: 6

Met Glu Pro Ser Ser Leu Glu Leu Pro Ala Asp Thr Val Gln Arg Ile
1               5                   10                  15

Ala Ala Glu Leu Lys Cys His Pro Thr Asp Glu Arg Val Ala Leu His
            20                  25                  30

Leu Asp Glu Glu Asp Lys Leu Arg His Phe Arg Glu Cys Phe Tyr Ile
        35                  40                  45

Pro Lys Ile Gln Asp Leu Pro Pro Val Asp Leu Ser Leu Val Asn Lys
    50                  55                  60

Asp Glu Asp Ala Ile Tyr Phe Asn Gly Asn Ser Leu Gly Leu Gln Pro
65                  70                  75                  80

Lys Met Val Lys Thr Tyr Leu Glu Glu Leu Asp Lys Trp Ala Lys
                 85                  90                  95

Ile Ala Ala Tyr Gly His Gln Val Gly Lys Arg Pro Trp Ile Thr Gly
            100                 105                 110

Asp Glu Ser Ile Val Gly Leu Met Lys Asp Ile Val Gly Ala Asn Glu
        115                 120                 125

Lys Glu Ile Ala Leu Met Asn Ala Leu Thr Val Asn Leu His Leu Leu
    130                 135                 140

Met Leu Ser Phe Phe Lys Pro Thr Pro Lys Arg Tyr Lys Ile Leu Leu
145                 150                 155                 160

Glu Ala Lys Ala Phe Pro Ser Asp His Tyr Ala Ile Glu Ser Gln Leu
                165                 170                 175

Gln Leu His Gly Leu Asn Ile Glu Glu Ser Met Arg Met Ile Lys Pro
            180                 185                 190

Arg Glu Gly Glu Thr Leu Arg Ile Glu Asp Ile Leu Glu Val Ile
        195                 200                 205

Glu Lys Glu Gly Asp Ser Ile Ala Val Ile Leu Phe Ser Gly Val His
    210                 215                 220

Tyr Tyr Thr Gly Gln His Phe Asn Ile Pro Ala Ile Thr Lys Ala Gly
225                 230                 235                 240

Gln Ala Lys Gly Cys Tyr Val Gly Phe Asp Leu Ala His Ala Val Gly
                245                 250                 255

Asn Val Glu Leu Tyr Leu His Asp Trp Gly Val Asp Phe Ala Cys Trp
            260                 265                 270

Cys Ser Tyr Lys Tyr Leu Asn Ala Gly Ala Gly Gly Ile Ala Gly Ala
        275                 280                 285

Phe Ile His Glu Lys His Ala His Thr Ile Lys Pro Ala Leu Val Gly
    290                 295                 300

Trp Phe Gly His Glu Leu Ser Thr Arg Phe Lys Met Asp Asn Lys Leu
305                 310                 315                 320

Gln Leu Ile Pro Gly Val Cys Gly Phe Arg Val Ser Asn Pro Pro Ile
                325                 330                 335

Leu Leu Val Cys Ser Leu His Ala Ser Leu Glu Ile Phe Lys Gln Ala
            340                 345                 350

Thr Met Lys Ala Leu Arg Lys Lys Ser Val Leu Leu Thr Gly Tyr Leu
        355                 360                 365

Glu Tyr Leu Ile Lys His Asn Tyr Gly Lys Asp Lys Ala Ala Thr Lys
    370                 375                 380

Lys Pro Val Val Asn Ile Ile Thr Pro Ser His Val Glu Glu Arg Gly
385                 390                 395                 400

Cys Gln Leu Thr Ile Thr Phe Asn Val Pro Asn Lys Asp Val Phe Gln
                405                 410                 415

Glu Leu Glu Lys Arg Gly Val Val Cys Asp Lys Arg Asn Pro Asn Gly
            420                 425                 430

Ile Arg Val Thr Pro Val Pro Leu Tyr Asn Ser Phe His Asp Val Tyr
        435                 440                 445

Lys Phe Thr Asn Leu Leu Thr Ser Ile Leu Asp Ser Ala Glu Thr Lys
    450                 455                 460

Asn
465

<210> SEQ ID NO 7
<211> LENGTH: 465
<212> TYPE: PRT

<213> ORGANISM: Artificial sequence
<220> FEATURE:
<223> OTHER INFORMATION: Synthetic polypeptide

<400> SEQUENCE: 7

Met Glu Pro Ser Ser Leu Glu Leu Pro Ala Asp Thr Val Gln Arg Ile
1               5                   10                  15

Ala Ala Glu Leu Lys Cys His Pro Thr Asp Glu Arg Val Ala Leu His
            20                  25                  30

Leu Asp Glu Asp Lys Leu Arg His Phe Arg Glu Cys Phe Tyr Ile
        35                  40                  45

Pro Lys Ile Gln Asp Leu Pro Pro Val Asp Leu Ser Leu Val Asn Lys
    50                  55                  60

Asp Glu Asp Ala Ile Tyr Phe Leu Gly Asn Ser Leu Gly Leu Gln Pro
65                  70                  75                  80

Lys Met Val Lys Thr Tyr Leu Glu Glu Leu Asp Lys Trp Ala Lys
                85                  90                  95

Ile Ala Ala Tyr Gly His Glu Val Gly Lys Arg Pro Trp Ile Thr Gly
                100                 105                 110

Asp Glu Ser Ile Val Gly Leu Met Lys Asp Ile Val Gly Ala Asn Glu
            115                 120                 125

Lys Glu Ile Ala Leu Met Asn Ser Leu Ser Val Asn Leu His Leu Leu
    130                 135                 140

Met Leu Ser Phe Phe Lys Pro Thr Pro Lys Arg Tyr Lys Ile Leu Leu
145                 150                 155                 160

Glu Ala Lys Ala Phe Pro Ser Asp His Tyr Ala Ile Glu Ser Gln Leu
                165                 170                 175

Gln Leu His Gly Leu Asn Ile Glu Glu Ser Met Arg Met Ile Lys Pro
            180                 185                 190

Arg Glu Gly Glu Glu Thr Leu Arg Ile Glu Asp Ile Leu Glu Val Ile
        195                 200                 205

Glu Lys Glu Gly Asp Ser Ile Ala Val Ile Leu Phe Ser Gly Val His
    210                 215                 220

Tyr Tyr Thr Gly Gln His Phe Asn Ile Pro Ala Ile Thr Lys Ala Gly
225                 230                 235                 240

Gln Ala Lys Gly Cys Tyr Val Gly Phe Asp Leu Ala His Ala Val Gly
                245                 250                 255

Asn Val Glu Leu Tyr Leu His Asp Trp Gly Val Asp Phe Ala Cys Trp
            260                 265                 270

Cys Ser Tyr Lys Tyr Leu Asn Ala Gly Ala Gly Gly Ile Ala Gly Ala
        275                 280                 285

Phe Ile His Glu Lys His Ala His Thr Ile Lys Pro Ala Leu Val Gly
    290                 295                 300

Trp Phe Gly His Glu Leu Ser Thr Arg Phe Lys Met Asp Asn Lys Leu
305                 310                 315                 320

Gln Leu Ile Pro Gly Val Cys Gly Phe Arg Ile Ser Asn Pro Pro Ile
                325                 330                 335

Leu Leu Val Cys Ser Leu His Ala Ser Leu Glu Ile Phe Lys Gln Ala
            340                 345                 350

Thr Met Lys Ala Leu Arg Lys Lys Ser Val Leu Thr Gly Tyr Leu
        355                 360                 365

Glu Tyr Leu Ile Lys His Asn Tyr Gly Lys Asp Lys Ala Ala Thr Lys
    370                 375                 380

Lys Pro Val Val Asn Ile Ile Thr Pro Ser His Val Glu Glu Arg Gly

```
                385                 390                 395                 400
Cys Gln Leu Thr Ile Thr Phe Asn Val Pro Asn Lys Asp Val Phe Gln
                    405                 410                 415

Glu Leu Glu Lys Arg Gly Val Val Cys Asp Lys Arg Asn Pro Asn Gly
                420                 425                 430

Ile Arg Val Thr Pro Val Pro Leu Tyr Asn Ser Phe His Asp Val Tyr
                435                 440                 445

Lys Phe Thr Asn Leu Leu Thr Ser Ile Leu Asp Ser Ala Glu Thr Lys
            450                 455                 460

Asn
465

<210> SEQ ID NO 8
<211> LENGTH: 465
<212> TYPE: PRT
<213> ORGANISM: Artificial sequence
<220> FEATURE:
<223> OTHER INFORMATION: Synthetic polypeptide

<400> SEQUENCE: 8

Met Glu Pro Ser Ser Leu Glu Leu Pro Ala Asp Thr Val Gln Arg Ile
1               5                   10                  15

Ala Ala Glu Leu Lys Cys His Pro Thr Asp Glu Arg Val Ala Leu His
                20                  25                  30

Leu Asp Glu Asp Lys Leu Arg His Phe Arg Glu Cys Phe Tyr Ile
                35                  40                  45

Pro Lys Ile Gln Asp Leu Pro Pro Val Asp Leu Ser Leu Val Asn Lys
50                  55                  60

Asp Glu Asn Ala Ile Tyr Phe Leu Gly Asn Ser Leu Gly Leu Gln Pro
65                  70                  75                  80

Lys Met Val Lys Thr Tyr Leu Glu Glu Glu Leu Asp Lys Trp Ala Lys
                85                  90                  95

Ile Ala Ser Tyr Gly His Glu Val Gly Lys Arg Pro Trp Ile Thr Gly
                100                 105                 110

Asp Glu Ser Ile Val Gly Leu Met Lys Asp Ile Val Gly Ala Asn Glu
            115                 120                 125

Lys Glu Ile Ala Leu Met Asn Gly Thr Thr Val Asn Leu His Leu Leu
130                 135                 140

Met Leu Ser Phe Phe Lys Pro Thr Pro Lys Arg Tyr Lys Ile Leu Leu
145                 150                 155                 160

Glu Ala Lys Ala Phe Pro Ser Asp His Tyr Ala Ile Glu Ser Gln Leu
                165                 170                 175

Gln Leu His Gly Leu Asn Ile Glu Glu Ser Met Arg Met Ile Lys Pro
            180                 185                 190

Arg Glu Gly Glu Glu Thr Leu Arg Ile Glu Asp Ile Leu Glu Val Ile
                195                 200                 205

Glu Lys Glu Gly Asp Ser Ile Ala Val Ile Leu Phe Ser Gly Val His
            210                 215                 220

Phe Tyr Thr Gly Gln His Phe Asn Ile Pro Ala Ile Thr Lys Ala Gly
225                 230                 235                 240

Gln Ala Lys Gly Cys Tyr Val Gly Phe Asp Leu Ala His Ala Val Gly
                245                 250                 255

Asn Val Glu Leu Tyr Leu His Asp Trp Gly Val Asp Phe Ala Cys Trp
            260                 265                 270

Cys Ser Tyr Lys Tyr Leu Asn Ala Gly Ala Gly Gly Ile Ala Gly Ala
```

```
                275                 280                 285
Phe Ile His Glu Lys His Ala His Thr Ile Lys Pro Ala Leu Val Gly
            290                 295                 300
Trp Leu Gly His Glu Leu Ser Thr Arg Phe Lys Met Asp Asn Lys Leu
305                 310                 315                 320
Gln Leu Ile Pro Gly Val Cys Gly Phe Arg Ile Ser Asn Pro Pro Ile
                325                 330                 335
Leu Leu Val Cys Ser Leu His Ala Ser Leu Glu Ile Phe Lys Gln Ala
            340                 345                 350
Thr Met Lys Ala Leu Arg Lys Lys Ser Val Leu Leu Thr Gly Tyr Leu
                355                 360                 365
Glu Tyr Leu Ile Lys His Asn Tyr Gly Lys Asp Lys Ala Ala Thr Lys
            370                 375                 380
Lys Pro Val Val Asn Ile Ile Thr Pro Ser His Val Glu Glu Arg Gly
385                 390                 395                 400
Cys Gln Leu Thr Ile Thr Phe Ser Val Pro Asn Lys Asp Val Phe Gln
                405                 410                 415
Glu Leu Glu Lys Arg Gly Val Val Cys Asp Lys Arg Asn Pro Asn Gly
            420                 425                 430
Ile Arg Val Thr Pro Val Pro Leu Tyr Asn Ser Phe His Asp Val Tyr
                435                 440                 445
Lys Phe Thr Asn Leu Leu Thr Ser Ile Leu Asp Ser Ala Glu Thr Lys
            450                 455                 460
Asn
465

<210> SEQ ID NO 9
<211> LENGTH: 4719
<212> TYPE: DNA
<213> ORGANISM: Escherichia coli

<400> SEQUENCE: 9
ccgacaccat cgaatggtgc aaaacctttc gcggtatggc atgatagcgc ccggaagaga       60
gtcaattcag ggtggtgaat gtgaaaccag taacgttata cgatgtcgca gagtatgccg      120
gtgtctctta tcagaccgtt tcccgcgtgg tgaaccaggc cagccacgtt tctgcgaaaa      180
cgcgggaaaa agtggaagcg gcgatggcgg agctgaatta cattcccaac cgcgtggcac      240
aacaactggc gggcaaacag tcgttgctga ttggcgttgc cacctccagt ctggccctgc      300
acgcgccgtc gcaaattgtc gcggcgatta aatctcgcgc cgatcaactg ggtgccagcg      360
tggtggtgtc gatggtagaa cgaagcggcg tcgaagcctg taaagcggcg gtgcacaatc      420
ttctcgcgca acgcgtcagt gggctgatca ttaactatcc gctggatgac caggatgcca      480
ttgctgtgga agctgcctgc actaatgttc cggcgttatt tcttgatgtc tctgaccaga      540
cacccatcaa cagtattatt ttctcccatg aagacggtac gcgactgggc gtggagcatc      600
tggtcgcatt gggtcaccag caaatcgcgc tgttagcggg cccattaagt tctgtctcgg      660
cgcgtctgcg tctggctggc tggcataaat atctcactcg caatcaaatt cagccgatag      720
cggaacggga aggcgactgg agtgccatgt ccggttttca acaaaccatg caaatgctga      780
atgagggcat cgttcccact gcgatgctgg ttgccaacga tcagatggcg ctgggcgcaa      840
tgcgcgccat taccgagtcc gggctgcgcg ttggtgcgga tatctcagta gtgggatacg      900
acgataccga agacagctca tgttatatcc cgccgttaac caccatcaaa caggattttc      960
gcctgctggg gcaaaccagc gtggaccgct tgctgcaact ctctcagggc caggcggtga     1020
```

```
agggcaatca gctgttgccc gtctcactgg tgaaaagaaa aaccaccctg gcgcccaata    1080
cgcaaaccgc ctctccccgc gcgttggccg attcattaat gcagctggca cgacaggttt    1140
cccgactgga aagcgggcag tgagcgcaac gcaattaatg taagttagct cactcattag    1200
gcacaattct catgtttgac agcttatcat cgactgcacg gtgcaccaat gcttctggcg    1260
tcaggcagcc atcggaagct gtggtatggc tgtgcaggtc gtaaatcact gcataattcg    1320
tgtcgctcaa ggcgcactcc cgttctggat aatgttttt gcgccgacat cataacggtt     1380
ctggcaaata ttctgaaatg agctgttgac aattaatcat cggctcgtat aatgtgtgga    1440
attgtgagcg gataacaatt tcacacagga acagccagt ccgtttaggt gttttcacga     1500
gcacttcacc aacaagtggt acctaatgca ttgataaaac cgcgcgaagg tgaggagacc    1560
ctgcggattg aggacatcct ggaggtgatc gagaaggagg cgacagtat cgcggtgata     1620
cttttcagcg gcgtgcattt ctacacgggc caacacttca atatcccggc cattaccaaa    1680
gccggccagc cgaaagggtg ctatgtaggc tttgatctgg cgcatgcagt gggcaacgtc    1740
gaactgtatc ttcatgattg gggcgttgat tttgcgtgct gccgcggatt acccgggctg    1800
caggcaagct tggcactggc cgtcgtttta caacgtcgtg actgggaaaa ccctggcgtt    1860
acccaactta atcgccttgc agcacatccc catttcgcca gctggcgtaa tagcgaagag    1920
gcccgcaccg atcgcccttc ccaacagttg cgcagcctga atggcgaatg gcagcttggc    1980
tgttttggcg gatgagataa gattttcagc ctgatacaga ttaaatcaga acgcagaagc    2040
ggtctgataa aacagaattt gcctggcggc agtagcgcgg tggtcccacc tgaccccatg    2100
ccgaactcag aagtgaaacg ccgtagcgcc gatggtagtg tggggtctcc ccatgcgaga    2160
gtagggaact gccaggcatc aaataaaacg aaaggctcag tcgaaagact gggcctttcg    2220
ttttatctgt tgtttgtcgg tgaacgctct cctgagtagg acaaatccgc cgggagcgga    2280
tttgaacgtt gcgaagcaac ggcccggagg gtggcgggca ggacgcccgc cataaactgc    2340
caggcatcaa attaagcaga aggccatcct gacggatggc cttttaacg tttacaattt     2400
caggtggcac ttttcgggga atgtgcgcg gaacccctat ttgtttattt ttctaaatac     2460
attcaaatat gtatccgctc atgtcgagac gttgggtgag gttccaactt tcaccataat    2520
gaaataagat cactaccggg cgtattttt gagttatcga gattttcagg agctaaggaa     2580
gctaaaatgg agaaaaaaat cactggatat accaccgttg atatatccca atggcatcgt    2640
aaagaacatt ttgaggcatt tcagtcagtt gctcaatgta cctataacca gaccgttcag    2700
ctggatatta cggccttttt aaagaccgta agaaaaata agcacaagtt ttatccggcc     2760
tttattcaca ttcttgcccg cctgatgaat gctcatccgg agttcgtat ggcaatgaaa     2820
gacggtgagc tggtgatatg ggatagtgtt caccctttgtt acaccgtttt ccatgagcaa    2880
actgaaacgt tttcatcgct ctggagtgaa taccacgacg atttccggca gtttctacac    2940
atatattcgc aagatgtggc gtgttacggt gaaaacctgg cctatttccc taaagggttt    3000
attgagaata tgttttttcgt ctcagccaat ccctgggtga gtttcaccag ttttgattta    3060
aacgtggcca atatggacaa cttcttcgcc cccgttttca ccatgggcaa atattatacg    3120
caaggcgaca aggtgctgat gccgctggcg attcaggttc atcatgccgt ttgtgatggc    3180
ttccatgtcg gcagaatgct taatgaatta caacagtact gcgatgagtg gcagggcggg    3240
gcgtaatttt tttaaggcag ttattggtgc ccttaaacgc ctggttgcta cgcctgaata    3300
agtgataata agcggatgaa tggcagaaat tcgaaagcaa attcgacccg gtcgtcggtt    3360
```

```
cagggcaggg tcgttaaata gccgcttatg tctattgctg gtttaccggt ttattgacta   3420
ccggaagcag tgtgaccgtg tgcttctcaa atgcctgagg ccagtttgct caggctctcc   3480
ccgtggaggt aataattaaa aggatctagg tgaagatcct ttttgataat ctcatgacca   3540
aaatccctta acgtgagttt tcgttccact gagcgtcaga ccccgtagaa aagatcaaag   3600
gatcttcttg agatcctttt tttctgcgcg taatctgctg cttgcaaaca aaaaaaccac   3660
cgctaccagc ggtggtttgt ttgccggatc aagagctacc aactcttttt ccgaaggtaa   3720
ctggcttcag cagagcgcag ataccaaata ctgtccttct agtgtagccg tagttaggcc   3780
accacttcaa gaactctgta gcaccgccta catacctcgc tctgctaatc ctgttaccag   3840
tggctgctgc cagtggcgat aagtcgtgtc ttaccgggtt ggactcaaga cgatagttac   3900
cggataaggc gcagcggtcg ggctgaacgg ggggttcgtg cacacagccc agcttggagc   3960
gaacgaccta caccgaactg agatacctac agcgtgagct atgagaaagc gccacgcttc   4020
ccgaagggag aaaggcggac aggtatccgg taagcggcag ggtcggaaca ggagagcgca   4080
cgagggagct tccaggggga aacgcctggt atctttatag tcctgtcggg tttcgccacc   4140
tctgacttga gcgtcgattt ttgtgatgct cgtcaggggg gcggagccta tggaaaaacg   4200
ccagcaacgc ggcctttttta cggttcctgg ccagttaagc cagtatacac tccgctatcg   4260
ctacgtgact gggtcatggc tgcgccccga cacccgccaa cacccgctga cgcgccctga   4320
cgggcttgtc tgctcccggc atccgcttac agacaagctg tgaccgtctc cgggagctgc   4380
atgtgtcaga ggttttcacc gtcatcaccg aaacgcgcga ggcagctgcg gtaaagctca   4440
tcagcgtggt cgtgcagcga ttcacagatg tctgcctgtt catccgcgtc cagctcgttg   4500
agtttctcca gaagcgttaa tgtctggctt ctgataaagc gggccatgtt aagggcggtt   4560
ttttcctgtt tggtcactga tgcctccgtg taagggggat ttctgttcat gggggtaatg   4620
ataccgatga aacgagagag gatgctcacg atacgggtta ctgatgatga acatgcccgg   4680
ttactggaac gttgtgaggg taaacaactg gcggtatgg                          4719
```

<210> SEQ ID NO 10
<211> LENGTH: 39
<212> TYPE: DNA
<213> ORGANISM: Artificial sequence
<220> FEATURE:
<223> OTHER INFORMATION: Synthetic primer

<400> SEQUENCE: 10

```
taaacaactg gcggtatggc cgacaccatc gaatggtgc                           39
```

<210> SEQ ID NO 11
<211> LENGTH: 50
<212> TYPE: DNA
<213> ORGANISM: Artificial sequence
<220> FEATURE:
<223> OTHER INFORMATION: Synthetic primer

<400> SEQUENCE: 11

```
gttttatcaa tgcattaggt accacttgtt ggtgaagtgc tcgtgaaaac                50
```

<210> SEQ ID NO 12
<211> LENGTH: 40
<212> TYPE: DNA
<213> ORGANISM: Artificial sequence
<220> FEATURE:
<223> OTHER INFORMATION: Synthetic primer

<400> SEQUENCE: 12
gtgtatactg gcttaactgg ccaggaaccg taaaaaggcc                                  40

<210> SEQ ID NO 13
<211> LENGTH: 52
<212> TYPE: DNA
<213> ORGANISM: Artificial sequence
<220> FEATURE:
<223> OTHER INFORMATION: Synthetic primer

<400> SEQUENCE: 13
ataggccgaa atcggcaaaa ggatctaggt gaagatcctt tttgataatc tc                   52

<210> SEQ ID NO 14
<211> LENGTH: 48
<212> TYPE: DNA
<213> ORGANISM: Artificial sequence
<220> FEATURE:
<223> OTHER INFORMATION: Synthetic primer

<400> SEQUENCE: 14 cttttttacgg ttcctggcca gttaagccag tatacactcc gctatcgc                       48

<210> SEQ ID NO 15
<211> LENGTH: 42
<212> TYPE: DNA
<213> ORGANISM: Artificial sequence
<220> FEATURE:
<223> OTHER INFORMATION: Synthetic primer

<400> SEQUENCE: 15
accattcgat ggtgtcggcc ataccgccag ttgtttaccc tc                              42

<210> SEQ ID NO 16
<211> LENGTH: 38
<212> TYPE: DNA
<213> ORGANISM: Artificial sequence
<220> FEATURE:
<223> OTHER INFORMATION: Synthetic primer

<400> SEQUENCE: 16
tgccgcggat tacccgggct gcaggcaagc ttggcact                                   38

<210> SEQ ID NO 17
<211> LENGTH: 42
<212> TYPE: DNA
<213> ORGANISM: Artificial sequence
<220> FEATURE:
<223> OTHER INFORMATION: Synthetic primer

<400> SEQUENCE: 17
cacctgaaat tgtaaacgtt aaaaaggcca tccgtcagga tg                              42

<210> SEQ ID NO 18
<211> LENGTH: 47
<212> TYPE: DNA
<213> ORGANISM: Artificial sequence
<220> FEATURE:
<223> OTHER INFORMATION: Synthetic primer

<400> SEQUENCE: 18
ctgacggatg gccttttaa cgtttacaat ttcaggtggc acttttc                          47

<210> SEQ ID NO 19
<211> LENGTH: 46
<212> TYPE: DNA

<213> ORGANISM: Artificial sequence
<220> FEATURE:
<223> OTHER INFORMATION: Synthetic primer

<400> SEQUENCE: 19
gatcttcacc tagatccttt taattattac ctccacgggg agagcc                46

<210> SEQ ID NO 20
<211> LENGTH: 37
<212> TYPE: DNA
<213> ORGANISM: Artificial sequence
<220> FEATURE:
<223> OTHER INFORMATION: Synthetic primer

<400> SEQUENCE: 20
gtggtaccta atgcattgat aaaaccgcgc gaaggtg                           37

<210> SEQ ID NO 21
<211> LENGTH: 38
<212> TYPE: DNA
<213> ORGANISM: Artificial sequence
<220> FEATURE:
<223> OTHER INFORMATION: Synthetic primer

<400> SEQUENCE: 21
agcccgggta atccgcggca gcacgcaaaa tcaacgcc                          38

<210> SEQ ID NO 22
<211> LENGTH: 465
<212> TYPE: PRT
<213> ORGANISM: Artificial sequence
<220> FEATURE:
<223> OTHER INFORMATION: Synthetic polypeptide

<400> SEQUENCE: 22

```
Met Glu Pro Ser Ser Leu Glu Leu Pro Ala Asp Thr Val Gln Arg Ile
1               5                   10                  15

Ala Ala Glu Leu Lys Cys His Pro Thr Asp Glu Arg Val Ala Leu His
                20                  25                  30

Leu Asp Glu Glu Asp Lys Leu Arg His Phe Arg Glu Cys Phe Tyr Ile
            35                  40                  45

Pro Lys Ile Gln Asp Leu Pro Pro Val Asp Leu Ser Leu Val Asn Lys
        50                  55                  60

Asp Glu Asn Ala Ile Tyr Phe Leu Gly Asn Ser Leu Gly Leu Gln Pro
65                  70                  75                  80

Lys Met Val Lys Thr Tyr Leu Glu Glu Leu Asp Lys Trp Ala Lys
                85                  90                  95

Ile Ala Ile Tyr Gly His Glu Val Gly Lys Arg Pro Trp Ile Thr Ala
                100                 105                 110

Asp Glu Ser Ile Val Gly Leu Met Lys Asp Ile Val Gly Ala Asn Glu
            115                 120                 125

Lys Glu Ile Ala Leu Met Asn Ala Leu Thr Val Asn Leu His Leu Leu
        130                 135                 140

Met Leu Ser Phe Phe Lys Pro Thr Pro Lys Arg Tyr Lys Ile Leu Leu
145                 150                 155                 160

Glu Ala Lys Ala Phe Pro Ser Asp His Tyr Ala Ile Glu Ser Gln Leu
                165                 170                 175

Gln Leu His Gly Leu Asn Ile Glu Glu Ser Met Arg Met Ile Lys Pro
            180                 185                 190

Arg Glu Gly Glu Glu Thr Leu Arg Ile Glu Asp Ile Leu Glu Val Ile
```

```
                195                 200                 205
Glu Lys Glu Gly Asp Ser Ile Ala Val Ile Leu Phe Ser Gly Val His
    210                 215                 220

Phe Tyr Thr Gly Gln His Phe Asn Ile Pro Ala Ile Thr Lys Ala Gly
225                 230                 235                 240

Gln Ala Lys Gly Cys Tyr Val Gly Phe Asp Leu Ala His Ala Val Gly
                245                 250                 255

Asn Val Glu Leu Tyr Leu His Asp Trp Gly Val Asp Phe Ala Cys Trp
            260                 265                 270

Cys Ser Tyr Lys Tyr Leu Asn Ala Gly Ala Gly Ile Ala Gly Ala
        275                 280                 285

Phe Ile His Glu Lys His Ala His Thr Ile Lys Pro Ala Leu Val Gly
290                 295                 300

Trp Tyr Gly His Glu Leu Ser Thr Arg Phe Lys Met Asp Asn Lys Leu
305                 310                 315                 320

Gln Leu Ile Pro Gly Val Cys Gly Phe Arg Ile Ser Asn Pro Pro Ile
                325                 330                 335

Leu Leu Val Cys Ser Leu His Ala Ser Leu Glu Ile Phe Lys Gln Ala
            340                 345                 350

Thr Met Lys Ala Leu Arg Lys Lys Ser Val Leu Leu Thr Gly Tyr Leu
        355                 360                 365

Glu Tyr Leu Ile Lys His Asn Tyr Gly Lys Asp Lys Ala Ala Thr Lys
    370                 375                 380

Lys Pro Val Val Asn Ile Ile Thr Pro Ser His Val Glu Glu Arg Gly
385                 390                 395                 400

Cys Gln Leu Thr Leu Thr Phe Asn Val Pro Asn Lys Asp Val Phe Gln
                405                 410                 415

Glu Leu Glu Lys Arg Gly Val Val Cys Asp Lys Arg Asn Pro Asn Gly
            420                 425                 430

Ile Arg Val Thr Pro Val Pro Leu Tyr Asn Ser Phe His Asp Val Tyr
        435                 440                 445

Lys Phe Thr Asn Leu Leu Thr Ser Ile Leu Asp Ser Ala Glu Thr Lys
    450                 455                 460

Asn
465

<210> SEQ ID NO 23
<211> LENGTH: 53
<212> TYPE: DNA
<213> ORGANISM: Artificial sequence
<220> FEATURE:
<223> OTHER INFORMATION: Synthetic primer

<400> SEQUENCE: 23
cactgtgtgg taccgaggta atacatgggc ggtcatcatc accaccatca tgg          53

<210> SEQ ID NO 24
<211> LENGTH: 50
<212> TYPE: DNA
<213> ORGANISM: Artificial sequence
<220> FEATURE:
<223> OTHER INFORMATION: Synthetic primer

<400> SEQUENCE: 24
cgagtcagcc cgggtaatcc gcggctagtt tttggtttcc gcactgtcca              50

<210> SEQ ID NO 25
```

<211> LENGTH: 1347
<212> TYPE: DNA
<213> ORGANISM: Artificial sequence
<220> FEATURE:
<223> OTHER INFORMATION: Synthetic oligonucleotide

<400> SEQUENCE: 25

| | |
|---|---|
| tctagaaata attttgttta actttaagga aaacattaaa ataaggaggt agcaaatggg | 60 |
| cggtcatcat caccaccatc atgggagcgg caccacccgc aacgattgcc tggcgctgga | 120 |
| tgcgcaggat agcctggcac cgctgcgtca gcagtttgcg ctgccggaag gtgttattta | 180 |
| tctggatggc aacagcctgg gtgcgcgtcc ggttgcggcg ctggcgcgtg cgcaggcggt | 240 |
| gattgcggaa gaatggggca acggcctgat tcgcagctgg aacagcgcgg gctggcgcga | 300 |
| tctgagcgaa cgcctgggca accgcctggc gaccctgatt ggcgcgcgcg atggcgaagt | 360 |
| ggtggtgacc gataccacca gcattaacct gtttaaagtg ctgagcgcgg cgctgcgcgt | 420 |
| gcaggcgacc cgcagcccgg aacgccgcgt gattgtgacc gaaaccagca actttccgac | 480 |
| cgatctgtat attgcggaag gcctggcgga tatgctgcag cagggctata ccctgcgcct | 540 |
| ggtggatagc ccggaagaac tgccgcaggc gattgatcag gataccgcgg tggtgatgct | 600 |
| gacccatgtg aactataaaa ccggctatat gcatgatatg caggcgctga ccgcgctgag | 660 |
| ccatgaatgc ggcgcgctgg cgatttggga tctggcgcat agcgcgggcg cggtgccggt | 720 |
| ggatctgcat caggcgggcg cggattatgc gattggctgc acctataaat atctgaacgg | 780 |
| cggcccgggc agccaggcgt ttgtgtgggt gagcccgcag ctgtgcgatc tggtgccgca | 840 |
| gccgctgtct ggttggtttg ccatagccg ccagtttgcg atggaaccgc gctatgaacc | 900 |
| gagcaacggc attgcgcgct atctgtgcgg cacccagccg attaccagcc tggcgatggt | 960 |
| ggaatgcggc ctggatgtgt ttgcgcagac cgatatggcg agcctgcgcc gcaaaagcct | 1020 |
| ggcgctgacc gatctgtttta ttgaactggt ggaacagcgc tgcgcggcgc atgaactgac | 1080 |
| cctggtgacc ccgcgcgaac atgcgaaacg cggcagccat gtgagctttg aacatccgga | 1140 |
| aggctatgcg gtgattcagg cgctgattga tcgcggcgtg attggcgatt atcgcgaacc | 1200 |
| gcgcattatg cgctttggct ttaccccgct gtataccacc tttaccgaag tgtgggatgc | 1260 |
| ggtgcagatt ctgggcgaaa ttctggatcg caaaacctgg gcgcaggcgc agtttcaggt | 1320 |
| gcgccatagc gtgacctagt aggatcc | 1347 |

<210> SEQ ID NO 26
<211> LENGTH: 465
<212> TYPE: PRT
<213> ORGANISM: Artificial sequence
<220> FEATURE:
<223> OTHER INFORMATION: Synthetic polypeptide

<400> SEQUENCE: 26

Met Glu Pro Ser Ser Leu Glu Leu Pro Ala Asp Thr Val Gln Arg Ile
1               5                   10                  15

Ala Ala Glu Leu Lys Cys His Pro Thr Asp Glu Arg Val Ala Leu His
                20                  25                  30

Leu Asp Glu Glu Asp Lys Leu Arg His Phe Arg Glu Cys Phe Tyr Ile
            35                  40                  45

Pro Lys Ile Gln Asp Leu Pro Pro Val Asp Leu Ser Leu Val Asn Lys
        50                  55                  60

Asp Glu Asn Ala Ile Tyr Phe Leu Gly Asn Ser Leu Gly Leu Gln Pro
65                  70                  75                  80

Lys Met Val Lys Thr Tyr Leu Glu Glu Leu Asp Lys Trp Ala Lys
                85                  90                  95

Ile Ala Ser Tyr Gly His Glu Val Gly Lys Arg Pro Trp Ile Thr Gly
            100                 105                 110

Asp Glu Ser Ile Val Gly Leu Met Lys Asp Ile Val Gly Ala Asn Glu
        115                 120                 125

Lys Glu Ile Ala Leu Met Asn Ala Leu Thr Val Asn Leu His Leu Leu
    130                 135                 140

Met Leu Ser Phe Phe Lys Pro Thr Pro Lys Arg Tyr Lys Ile Leu Leu
145                 150                 155                 160

Glu Ala Lys Ala Phe Pro Ser Asp His Tyr Ala Ile Glu Ser Gln Leu
                165                 170                 175

Gln Leu His Gly Leu Asn Ile Glu Glu Ser Met Arg Met Ile Lys Pro
            180                 185                 190

Arg Glu Gly Glu Thr Leu Arg Ile Glu Asp Ile Leu Glu Val Ile
        195                 200                 205

Glu Lys Glu Gly Asp Ser Ile Ala Val Ile Leu Phe Ser Gly Val His
    210                 215                 220

Phe Tyr Thr Gly Gln His Phe Asn Ile Pro Ala Ile Thr Lys Ala Gly
225                 230                 235                 240

Gln Ala Lys Gly Cys Tyr Val Gly Phe Asp Leu Ala His Ala Val Gly
                245                 250                 255

Asn Val Glu Leu Tyr Leu His Asp Trp Gly Val Asp Phe Ala Cys Trp
            260                 265                 270

Cys Ser Tyr Lys Tyr Leu Asn Ala Gly Ala Gly Gly Ile Ala Gly Ala
        275                 280                 285

Phe Ile His Glu Lys His Ala His Thr Ile Lys Pro Ala Leu Val Gly
    290                 295                 300

Trp Leu Gly His Glu Leu Ser Thr Arg Phe Lys Met Asp Asn Lys Leu
305                 310                 315                 320

Gln Leu Ile Pro Gly Val Cys Gly Phe Arg Ile Ser Asn Pro Pro Ile
                325                 330                 335

Leu Leu Val Cys Ser Leu His Ala Ser Leu Glu Ile Phe Lys Gln Ala
            340                 345                 350

Thr Met Lys Ala Leu Arg Lys Lys Ser Val Leu Leu Thr Gly Tyr Leu
        355                 360                 365

Glu Tyr Leu Ile Lys His Asn Tyr Gly Lys Asp Lys Ala Ala Thr Lys
    370                 375                 380

Lys Pro Val Val Asn Ile Ile Thr Pro Ser His Val Glu Glu Arg Gly
385                 390                 395                 400

Cys Gln Leu Thr Ile Thr Phe Ser Val Pro Asn Lys Asp Val Phe Gln
                405                 410                 415

Glu Leu Glu Lys Arg Gly Val Val Cys Asp Lys Arg Asn Pro Asn Gly
            420                 425                 430

Ile Arg Val Thr Pro Val Pro Leu Tyr Asn Ser Phe His Asp Val Tyr
        435                 440                 445

Lys Phe Thr Asn Leu Leu Thr Ser Ile Leu Asp Ser Ala Glu Thr Lys
    450                 455                 460

Asn
465

<210> SEQ ID NO 27
<211> LENGTH: 1398
<212> TYPE: DNA

<213> ORGANISM: Artificial sequence
<220> FEATURE:
<223> OTHER INFORMATION: Synthetic oligonucleotide

<400> SEQUENCE: 27

```
atggaaccga gctcccttga acttccggcc gataccgtgc aacggatagc ggcggaattg      60
aaatgtcacc cgaccgacga acgcgtcgcg ttacatctgg atgaggaaga caagctgcgt     120
cacttccgcg agtgcttta cattccgaaa attcaggatc tgccgccagt ggacttgagc     180
ctggtcaaca aagacgagaa cgccatctac ttcctgggca atagcctggg cctgcaacca     240
aagatggtga aaacctatct tgaggaggag cttgacaaat gggcgaagat cgcgatctac     300
ggccatgaag tcggcaagcg tccctggatt accgctgatg agtcaatcgt tggcttgatg     360
aaggatatcg tcggcgcgaa cgagaaagaa attgcgctga tgaacgcgct gaccgtgaat     420
ctgcatctgc tgatgctgtc attctttaag cccaccccga agcgctacaa aatcctgctg     480
gaagcgaaag cgtttcccag cgatcattat gcgatagaaa gccagctgca actgcacggc     540
ctgaatatcg aggagagcat gcgtatgata aaaccgcgcg aaggtgagga accctgcgg     600 attgaggaca tcctggaggt gatcgagaag gagggcgaca gtatcgcggt gatacttttc     660
agcggcgtgc atttctacac gggccaacac ttcaatatcc cggccattac caaagccggc     720
caggcgaaag ggtgctatgt aggctttgat ctggcgcatg cagtgggcaa cgtcgaactg     780
tatcttcatg attggggcgt tgattttgcg tgctggtgca gctataagta tctgaatgcc     840
ggggccggtg ggattgcggg agcctttatt catgagaaac acgcgcatac cattaaaccg     900
gcgctggttg gctggtatgg gcacgaactg agcacccgct tcaagatgga taacaaactg     960
caattgattc cgggcgtgtg cggctttcgt aatagcaacc cccgattct gctggtctgc    1020 agcctgcacg cgtctctgga gattttcaag caggcgacca tgaaagcgct gcgtaagaaa    1080
agtgtgcttc tgacgggcta cctggagtac ctgataaagc acaactacgg caaggataag    1140
gcggccacga gaagccggt tgtgaacatt atcaccccgt ctcatgtgga agaacgtggc    1200
tgccaactga cgcttacgtt caacgtgcca aacaaggacg tgttccaaga gctggagaag    1260
cgtggcgtgg tgtgtgataa acgtaatccg aatggcattc gtgtgacgcc tgtgccgctg    1320
tacaacagct tccacgacgt gtataagttc accaacctgc tgacgagcat tctggacagt    1380
gcggaaacca aaaactag                                                 1398
```

<210> SEQ ID NO 28
<211> LENGTH: 1398
<212> TYPE: DNA
<213> ORGANISM: Artificial sequence
<220> FEATURE:
<223> OTHER INFORMATION: Synthetic oligonucleotide

<400> SEQUENCE: 28

```
atggaaccga gctcccttga acttccggcc gataccgtgc aacggatagc ggcggaattg      60
aaatgtcacc cgaccgacga acgcgtcgcg ttacatctgg atgaggaaga caagctgcgt     120
cacttccgcg agtgcttta cattccgaaa attcaggatc tgccgccagt ggacttgagc     180
ctggtcaaca aagacgagaa cgccatctac ttcctgggca atagcctggg cctgcaacca     240
aagatggtga aaacctatct tgaggaggag cttgacaaat gggcgaagat cgcgatctac     300
ggccatgaag tcggcaagcg tccctggatt accgctgatg agtcaatcgt tggcttgatg     360
aaggatatcg tcggcgcgaa cgagaaagaa attgcgctga tgaacgcgct gaccgtgaat     420
ctgcatctgc tgatgctgtc attctttaag cccaccccga agcgctacaa aatcctgctg     480
```

```
gaagcgaaag cgtttcccag cgatcattat gcgatagaaa gccagctgca actgcacggc    540
ctgaatatcg aggagagcat gcgtatgata gaaccgcgcg aaggtgagga gaccctgcgg    600
attgaggaca tcctggaggt gatcgagaag gagggcgaca gtatcgcggt gatacttttc    660
agcggcgtgc atttctacac gggccaacac ttcaatatcc cggccattac caaagccggc    720
caggcgaaag ggtgctatgt aggctttgat ctggcgcatg cagtgggcaa cgtcgaactg    780
tatcttcatg attggggcgt tgattttgcg tgctggtgca gctataagta tctgaatgcc    840
ggggccggtg ggattgcggg agcctttatt catgagaaac acgcgcatac cattaaaccg    900
gcgctggttg gctggtatgg gcacgaactg agcacccgct tcaagatgga taacaaactg    960
caattgattc cgggcgtgtg cggctttcgt attagcaacc ccccgattct gctggtctgc   1020
agcctgcacg cgtctctgga gattttcaag caggcgacca tgaaagcgct gcgtaagaaa   1080
agtgtgcttc tgacgggcta cctggagtac ctgataaagc acaactacgg caaggataag   1140
tcggccacga agaagccggt tgtgaacatt atcacccccgt ctcatgtgga agaacgtggc   1200
tgccaactga cgcttacgtt caacgtgcca aacaaggacg tgttccaaga gctggagaag   1260
cgtggcgtgg tgtgtgataa acgtaatccg aatggcattc gtgtgacgcc tgtgccgctg   1320
tacaacagct ccacgacgt gtataagttc accaacctgc tgacgagcat tctggacagt   1380
gcggaaacca aaaactag                                                  1398

<210> SEQ ID NO 29
<211> LENGTH: 1398
<212> TYPE: DNA
<213> ORGANISM: Artificial sequence
<220> FEATURE:
<223> OTHER INFORMATION: Synthetic oligonucleotide

<400> SEQUENCE: 29
atggaaccga gctcccttga acttccggcc gataccgtgc gacggatagc ggcggaattg     60
aaatgtcacc cgaccgacga acgcgtcgcg ttacatctgg acgaggaaga caagctgcgt    120
cacttccgcg agtgctttta cattccgaaa attcaggatc tgccgccagt ggacttgagc    180
ctggtcaaca aagacgagaa cgccatctac ttcctgggta tagcctgggg cctgcaacca    240
aagatggtga aaacctatct tgaggaggag cttgacaaat gggcgaagat cgcgatctac    300
ggccatgaag tcggcaagcg tccctggatt accgctgatg agtcaatcgt tggcttgatg    360
aaggatatcg tcggcgcgaa cgagaaagaa attgcgctga tgaacgcgct gaccgtgaat    420
ctgcatctgc tgatgctgtc attctttaag cccaccccga gcgctacaa atcctgctg     480 gaagcgaaag cgtttcccag cgatcattat gcgatagaaa gccagctgca actgcacggc    540
ctgaatatcg aggagagcat gcgtataata aaaccgcgcg aaggtgagga gaccctgcgg    600
attgaggaca tcctggaggt gatcgagaag gagggcgaca gtatcgcggt gatacttttc    660
agcggcgtgc atttctacac gggccaatac ttcaatatcc cggccattac caaagccggc    720
caggcgaaag ggtgctatgt aggctttgat ctggcgcatg cagtgggcaa cgtcgaactg    780
tatcttcatg attggggcgt tgattttgcg tgctggtgca gctataagta tctgaatgcc    840
ggggccggtg ggattgcggg agcctttatt catgagaaac atgcgcatac cattaaaccg    900
gcgctggttg gctggtatgg gcacgaactg agcacccgct tcaagatgga taacaaactg    960
caattgattc cgggcgtgtg cggctttcgt aatagcaacc ccccgattct gctggtctgc   1020
agcctgcacg cgtctctgga gattttcaag caggcgacta tgaaagcgct gcgtaagaaa   1080
```

```
agtgtgcttc tgacgggcta tctggagtac ctgataaagc acaactacgg caaggataag    1140
gcggccacga agaagccggt tgtgaacatt atcaccccgt ctcatgtgga agaacgtggc    1200
tgccaactga cgcttacgtt caacgtgcca acaaggacg tgttccaaga gctggagaag     1260
cgtggcgtgg tgtgtgataa acgtaatccg aatggcattc gtgtgacgcc tgtgccgctg    1320
tacaacagct ccacgacgt gtataagttc accaacctgc tgacgagcat tctggacagt    1380
gcggaaacca aaaactag                                                  1398

<210> SEQ ID NO 30
<211> LENGTH: 1398
<212> TYPE: DNA
<213> ORGANISM: Artificial sequence
<220> FEATURE:
<223> OTHER INFORMATION: Synthetic oligonucleotide

<400> SEQUENCE: 30
atggaaccga gctcccttga acttccggcc gataccgtgc aacggatagc ggcggaattg     60
aaatgtcacc cgaccgacga acgcgtcgcg ttacatctgg atgaggaaga caagctgcgt    120
cacttccgcg agtgctttta cattccgaaa attcaggatc tgccgccagt ggacttgagc    180
ctggtcaaca aagacgagaa tgccatctat ttcctgggca atagcctggg cctgcaacca    240
aagatggtga aaacctatct tgaggaggag cttgacaaat gggcgaagat cgcggcctac    300
ggccatgagg tcggcaagcg tccctggatt accggcgatg agtcaatcgt tggcttgatg    360
aaggatatcg tcggcgcgaa cgagaaagaa attgcgctga tgaacgcctt atctgtgaat    420
ctgcatctgc tgatgctgtc attctttaag cccaccccga agcgctacaa aatcctgctg    480
gaagcgaaag cgtttcccag cgatcattat gcgatagaaa gccagctgca actgcacggc    540
ctgaatatcg aggagagcat gcgtatgata aaaccgcgcg aaggtgagga gaccctgcgg    600
attgaggaca tcctggaggt gatcgagaag gagggcgaca gtatcgcggt gatacttttc    660
tctggcgtga attattacac gggccaacac ttcaatatcc cggccattac caaagccggc    720
caggcgaaag ggtgctatgt aggctttgat ctggcgcatg cagtgggcaa cgtcgaactg    780
tatcttcatg attggggcgt tgattttgcg tgctggtgca gctataagta tctgaatgcc    840
ggggccggtg ggattgcggg agcctttatt catgagaaac acgcgcatac cattaaaccg    900
gcgctggttg gctggtgggg gcacgaactg agcacccgct tcaagatgga taacaaactg    960
caattgattc cgggcgtgtg cggctttcgt attagcaccc cgccgattct gctggtctgc   1020
agcctgcacg cgtctctgga gattttcaag caggcgacca tgaaagcgct gcgtaagaaa   1080
agtgtgcttc tgacgggcta cctggagtac ctgataaagc acaactacgg caaggataag   1140
gcggccacga agaagccggt tgtgaacatt atcaccccgt ctcatgtgga agaacgtggc   1200
tgccagctga cgataacgtt caacgtgcca acaaggacg tgttccaaga gctggagaag    1260
cgtggcgtgg tgtgtgataa acgtaatccg aatggcattc gtgtgacgcc tgtgccgctg   1320
tacaacagct ccacgacgt gtataagttc accaacctgc tgacgagcat tctggacagt    1380
gcggaaacca aaaactag                                                 1398

<210> SEQ ID NO 31
<211> LENGTH: 1398
<212> TYPE: DNA
<213> ORGANISM: Artificial sequence
<220> FEATURE:
<223> OTHER INFORMATION: Synthetic oligonucleotide

<400> SEQUENCE: 31
```

```
atggaaccga gctcccttga acttccggcc gataccgtgc aacggatagc ggcggaattg      60
aaatgtcacc cgaccgacga acgcgtcgcg ttacatctgg atgaggaaga caagctgcgt     120
cacttccgcg agtgctttta cattccgaaa attcaggatc tgccgccagt ggacttgagc     180
ctggtcaaca aagacgagga tgccatctat ttcaatggca atagcctggg cctgcaacca     240
aagatggtga aaacctatct tgaggaggag cttgacaaat gggcgaagat cgcggcctac     300
ggccatcagg tcggcaagcg tccctggatt accggcgatg agtcaatcgt tggcttgatg     360
aaggatatcg tcggcgcgaa cgagaaagaa attgcgctga tgaacgcctt aactgtgaat     420
ctgcatctgc tgatgctgtc attctttaag cccaccccga agcgctacaa aatcctgctg     480
gaagcgaaag cgtttcccag cgatcattat gcgatagaaa gccagctgca actgcacggc     540
ctgaatatcg aggagagcat gcgtatgata aaaccgcgcg aaggtgagga gaccctgcgg     600
attgaggaca tcctggaggt gatcgagaag gagggcgaca gtatcgcggt gatactttc     660 tctggcgtgc attattacac gggccaacac ttcaatatcc cggccattac caaagccggc     720
caggcgaaag ggtgctatgt aggctttgat ctggcgcatg cagtgggcaa cgtcgaactg     780
tatcttcatg attggggcgt tgattttgcg tgctggtgca gctataagta tctgaatgcc     840
ggggccggtg ggattgcggg agcctttatt catgagaaac acgcgcatac cattaaaccg     900
gcgctggttg gctggtttgg gcacgaactg agcacccgct tcaagatgga taacaaactg     960
caattgattc cgggcgtgtg cggctttcgt gttagcaacc cgccgattct gctggtctgc    1020
agcctgcacg cgtctctgga gattttcaag caggcgacca tgaaagcgct gcgtaagaaa    1080
agtgtgcttc tgacgggcta cctggagtac ctgataaagc acaactacgg caaggataag    1140
gcggccacga gaagccggt tgtgaacatt atcaccccgt ctcatgtgga agaacgtggc    1200
tgccagctga cgataacgtt caacgtgcca acaaggacg tgttccaaga gctggagaag    1260
cgtggcgtgg tgtgtgataa acgtaatccg aatggcattc gtgtgacgcc tgtgccgctg    1320
tacaacagct tccacgacgt gtataagttc accaacctgc tgacgagcat tctggacagt    1380
gcggaaacca aaaactag                                                  1398
```

<210> SEQ ID NO 32
<211> LENGTH: 1398
<212> TYPE: DNA
<213> ORGANISM: Artificial sequence
<220> FEATURE:
<223> OTHER INFORMATION: Synthetic oligonucleotide

<400> SEQUENCE: 32

```
atggaaccga gctcccttga acttccggcc gataccgtgc aacggatagc ggcggaattg      60
aaatgtcacc cgaccgacga acgcgtcgcg ttacatctgg atgaggaaga caagctgcgt     120
cacttccgcg agtgctttta cattccgaaa attcaggatc tgccgccagt ggacttgagc     180
ctggtcaaca aagacgagga tgccatctat ttcctgggca atagcctggg cctgcaacca     240
aagatggtga aaacctatct tgaggaggag cttgacaaat gggcgaagat cgcggcctac     300
ggccatgagg tcggcaagcg tccctggatt accggcgatg agtcaatcgt tggcttgatg     360
aaggatatcg tcggcgcgaa cgagaaagaa attgcgctga tgaactcctt atctgtgaat     420
ctgcatctgc tgatgctgtc attctttaag cccaccccga agcgctacaa aatcctgctg     480
gaagcgaaag cgtttcccag cgatcattat gcgatagaaa gccagctgca actgcacggc     540
ctgaatatcg aggagagcat gcgtatgata aaaccgcgcg aaggtgagga gaccctgcgg     600
```

```
attgaggaca tcctggaggt gatcgagaag gagggcgaca gtatcgcggt gatacttttc      660
tctggcgtgc attattacac gggccaacac ttcaatatcc cggccattac caaagccggc      720
caggcgaaag ggtgctatgt aggctttgat ctggcgcatg cagtgggcaa cgtcgaactg      780
tatcttcatg attggggcgt tgattttgcg tgctggtgca gctataagta tctgaatgcc      840
ggggccggtg ggattgcggg agcctttatt catgagaaac acgcgcatac cattaaaccg      900
gcgctggttg gctggtttgg gcacgaactg agcacccgct tcaagatgga taacaaactg      960
caattgattc cgggcgtgtg cggctttcgt attagcaacc cgccgattct gctggtctgc     1020
agcctgcacg cgtctctgga gattttcaag caggcgacca tgaaagcgct gcgtaagaaa     1080
agtgtgcttc tgacgggcta cctggagtac ctgataaagc acaactacgg caaggataag     1140
gcggccacga gaagccggt tgtgaacatt atcacccccgt ctcatgtgga agaacgtggc     1200
tgccagctga cgataacgtt caacgtgcca aacaaggacg tgttccaaga gctggagaag     1260
cgtggcgtgg tgtgtgataa acgtaatccg aatggcattc gtgtgacgcc tgtgccgctg     1320
tacaacagct tccacgacgt gtataagttc accaacctgc tgacgagcat tctggacagt     1380
gcggaaaacca aaaactag                                                  1398

<210> SEQ ID NO 33
<211> LENGTH: 1398
<212> TYPE: DNA
<213> ORGANISM: Artificial sequence
<220> FEATURE:
<223> OTHER INFORMATION: Synthetic oligonucleotide

<400> SEQUENCE: 33
atggaaccga gctcccttga acttccggcc gataccgtgc aacggatagc ggcggaattg       60
aaatgtcacc cgaccgacga acgcgtcgcg ttacatctgg atgaggaaga caagctgcgt      120
cacttccgcg agtgctttta cattccgaaa attcaggatc tgccgccagt ggacttgagc      180
ctggtcaaca aagacgagaa cgccatctac ttcctgggca atagcctggg cctgcaacca      240
aagatggtga aacctatct tgaggaggag cttgacaaat gggcgaagat cgcgagctac      300
ggccatgaag tcggcaagcg tccctggatt accggcgatg agtcaatcgt tggcttgatg      360
aaggatatcg tcggcgcgaa cgagaaagaa attgcgctga tgaacggcac gaccgtgaat      420
ctgcatctgc tgatgctgtc attctttaag cccacccccga agcgctacaa aatcctgctg      480
gaagcgaaag cgtttcccag cgatcattat gcgatagaaa gccagctgca actgcacggc      540
ctgaatatcg aggagagcat gcgtatgata aaaccgcgcg aaggtgagga gacccctgcgg      600
attgaggaca tcctggaggt gatcgagaag gagggcgaca gtatcgcggt gatacttttc      660
agcggcgtgc atttctacac gggccaacac ttcaatatcc cggccattac caaagccggc      720
caggcgaaag ggtgctatgt aggctttgat ctggcgcatg cagtgggcaa cgtcgaactg      780
tatcttcatg attggggcgt tgattttgcg tgctggtgca gctataagta tctgaatgcc      840
ggggccggtg ggattgcggg agcctttatt catgagaaac acgcgcatac cattaaaccg      900
gcgctggttg gctggctggg gcacgaactg agcacccgct tcaagatgga taacaaactg      960
caattgattc cgggcgtgtg cggctttcgt attagcaacc ccccgattct gctggtctgc     1020
agcctgcacg cgtctctgga gattttcaag caggcgacca tgaaagcgct gcgtaagaaa     1080
agtgtgcttc tgacgggcta cctggagtac ctgataaagc acaactacgg caaggataag     1140
gcggccacga gaagccggt tgtgaacatt atcacccccgt ctcatgtgga agaacgtggc     1200
tgccaactga cgataacgtt cagcgtgcca aacaaggacg tgttccaaga gctggagaag     1260
```

```
cgtggcgtgg tgtgtgataa acgtaatccg aatggcattc gtgtgacgcc tgtgccgctg    1320
tacaacagct tccacgacgt gtataagttc accaacctgc tgacgagcat tctggacagt    1380
gcggaaacca aaaactag                                                   1398

<210> SEQ ID NO 34
<211> LENGTH: 1497
<212> TYPE: DNA
<213> ORGANISM: Artificial sequence
<220> FEATURE:
<223> OTHER INFORMATION: Synthetic oligonucleotide

<400> SEQUENCE: 34
tctagaaata attttgttta actttaagga caaatcagga cacagttaag gaggtaaaat      60
atgggcggtc atcatcacca ccatcatggg agcggcgaac cgagctccct tgaacttccg     120
gccgataccg tgcaacggat agcggcggaa ttgaaatgtc acccgaccga cgaacgcgtc     180
gcgttacatc tggatgagga agacaagctg cgtcacttcc gcgagtgctt ttacattccg     240
aaaattcagg atctgccgcc agtggacttg agcctggtca acaaagacga gaacgccatc     300
tacttcctgg gcaatagcct gggcctgcaa ccaaagatgg tgaaaaccta tcttgaggag     360
gagcttgaca atgggcgaa gatcgcggcc tacggccatg aagtcggcaa gcgtccctgg     420
attaccggcg atgagtcaat cgttggcttg atgaaggata tcgtcggcgc gaacgagaaa     480
gaaattgcgc tgatgaacgc gctgaccgtg aatctgcatc tgctgatgct gtcattcttt     540
aagcccaccc cgaagcgcta caaaatcctg ctggaagcga aagcgttttcc cagcgatcat     600 tatgcgatag aaagccagct gcaactgcac ggcctgaata tcgaggagag catgcgtatg     660
ataaaaccgc gcgaaggtga ggagaccctg cggattgagg acatcctgga ggtgatcgag     720
aaggagggcg acagtatcgc ggtgatactt ttcagcggcg tgcatttcta cacgggccaa     780
cacttcaata tcccggccat taccaaagcc ggccaggcga aagggtgcta tgtaggcttt     840
gatctggcgc atgcagtggg caacgtcgaa ctgtatcttc atgattgggg cgttgatttt     900
gcgtgctggt gcagctataa gtatctgaat gccggggccg gtgggattgc gggagccttt     960
attcatgaga aacacgcgca taccattaaa ccggcgctgg ttggctggtt tgggcacgaa    1020
ctgagcaccc gcttcaagat ggataacaaa ctgcaattga ttccgggcgt gtgcggcttt    1080
cgtattagca accccccgat tctgctggtc tgcagcctgc acgcgtctct ggagattttc    1140
aagcaggcga ccatgaaagc gctgcgtaag aaaagtgtgc ttctgacggg ctacctggag    1200
tacctgataa agcacaacta cggcaaggat aaggcggcca cgaagaagcc ggttgtgaac    1260
attatcaccc cgtctcatgt ggaagaacgt ggctgccaac tgacgataac gttcagcgtg    1320
ccaaacaagg acgtgttcca agagctggag aagcgtggcg tggtgtgtga taaacgtaat    1380
ccgaatggca ttcgtgtggc gcctgtgccg ctgtacaaca gcttccacga cgtgtataag    1440
ttcaccaacc tgctgacgag cattctggac agtgcggaaa ccaaaaacta gggatcc       1497
```